(12) United States Patent
Ma et al.

(10) Patent No.: US 8,268,572 B2
(45) Date of Patent: Sep. 18, 2012

(54) METHODS TO IDENTIFY INHIBITORS OF RUNX1-MEDIATED EXPRESSION OF NOCICEPTIVE RECEPTORS AND ION CHANNELS

(75) Inventors: Qiufu Ma, Needham, MA (US); Chih-Li Chen, Taipei Hsien (TW); Clifford J. Woolf, Newton, MA (US); Daniel C. Broom, Branford, CT (US)

(73) Assignees: Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 763 days.

(21) Appl. No.: 11/884,800

(22) PCT Filed: Mar. 3, 2006

(86) PCT No.: PCT/US2006/007578
§ 371 (c)(1),
(2), (4) Date: Mar. 20, 2009

(87) PCT Pub. No.: WO2006/096498
PCT Pub. Date: Sep. 14, 2006

(65) Prior Publication Data
US 2009/0170079 A1 Jul. 2, 2009

Related U.S. Application Data

(60) Provisional application No. 60/658,824, filed on Mar. 4, 2005.

(51) Int. Cl.
*C12Q 1/68* (2006.01)
*G01N 33/53* (2006.01)
*G01N 33/567* (2006.01)

(52) U.S. Cl. ........ 435/7.2; 435/6.1; 435/6.13; 435/6.16; 435/6.17

(58) Field of Classification Search .................... None
See application file for complete search history.

(56) References Cited

U.S. PATENT DOCUMENTS
2004/0146986 A1 7/2004 Bae et al.

OTHER PUBLICATIONS

Alessandri AJ et al., ETV6 (TEL)-AML1 pre-B acute lymphoblastic leukaemia cells are associated with a distinct antigen-presenting phenotype. *Br J Haematol.* Feb. 2002;116(2):266-72.
Bäckstrom S et al., The RUNX1 Runt domain at 1.25A resolution: a structural switch and specifically bound chloride ions modulate DNA binding. *J Mol Biol.* Sep. 13, 2002;322(2):259-72.
Bandell M et al., Noxious cold ion channel TRPA1 is activated by pungent compounds and bradykinin. *Neuron.* Mar. 25, 2004;41(6):849-57.
Chen CC et al., A P2X purinoceptor expressed by a subset of sensory neurons. *Nature.* Oct. 5, 1995;377(6548):428-31.
Chen CL et al., Runx1 determines nociceptive sensory neuron phenotype and is required for thermal and neuropathic pain. *Neuron.* Feb. 2, 2006;49(3):365-77.
Corey DP et al., TRPA1 is a candidate for the mechanosensitive transduction channel of vertebrate hair cells. *Nature.* Dec. 9, 2004;432(7018):723-30. Epub Oct. 13, 2004.
De Bruijn MF et al., Core-binding factors in hematopoiesis and immune function. *Oncogene.* May 24, 2004;23(24):4238-48.
Decosterd I et al., Spared nerve injury: an animal model of persistent peripheral neuropathic pain. *Pain.* Aug. 2000;87(2):149-58.
Dib-Hajj SDet al., NaN, a novel voltage-gated Na channel, is expressed preferentially in peripheral sensory neurons and down-regulated after axotomy. *Proc Natl Acad Sci U S A.* Jul. 21, 1998;95(15):8963-8.
Dong X et al., A diverse family of GPCRs expressed in specific subsets of nociceptive sensory neurons. *Cell.* Sep. 7, 2001;106(5):619-32.
Grazzini E et al., Sensory neuron-specific receptor activation elicits central and peripheral nociceptive effects in rats. *Proc Natl Acad Sci U S A.* May 4, 2004;101(18):7175-80. Epub Apr. 26, 2004.
GenBank accession No. A94121, downloaded Mar. 19, 2009.
GenBank accession No. AB154412, downloaded Mar. 19, 2009.
GenBank accession No. AF025841, downloaded Mar. 19, 2009.
GenBank accession No. AF126739, downloaded Mar. 19, 2009.
GenBank accession No. AF193030, downloaded Mar. 19, 2009.
GenBank accession No. AL663116, downloaded Mar. 19, 2009.
GenBank accession No. AY042209, downloaded Mar. 19, 2009.
GenBank accession No. D13802, downloaded Mar. 19, 2009.
GenBank accession No. NM_001001445, downloaded Mar. 19, 2009.
GenBank accession No. NM_001001890, downloaded Mar. 19, 2009.
GenBank accession No. NM_001754, downloaded Mar. 19, 2009.
GenBank accession No. NM_002559, downloaded Mar. 19, 2009.
GenBank accession No. NM_003305, downloaded Mar. 19, 2009.
GenBank accession No. NM_011706, downloaded Mar. 19, 2009.
GenBank accession No. NM_014139, downloaded Mar. 19, 2009.
GenBank accession No. NM_016113, downloaded Mar. 19, 2009.
GenBank accession No. NM_019510, downloaded Mar. 19, 2009.
GenBank accession No. NM_024080, downloaded Mar. 19, 2009.
GenBank accession No. NM_080706, downloaded Mar. 19, 2009.
GenBank accession No. NM_134252, downloaded Mar. 19, 2009.
GenBank accession No. NM_145526, downloaded Mar. 19, 2009.
GenBank accession No. NM_198923, downloaded Mar. 19, 2009.
GenBank accession No. NM_203490, downloaded Mar. 19, 2009.
GenBank accession No. Q03347, downloaded Mar. 19, 2009.
Growney JD et al., Loss of Runx1 perturbs adult hematopoiesis and is associated with a myeloproliferative phenotype. *Blood* Jul. 15, 2005;106(2):494-504. Epub Mar 22, 2005.
Hunt SP et al., The molecular dynamics of pain control, *Nat Rev Neurosci.*, Feb. 2001;2(2):83-91.
Inoue K et al., Runx3 controls the axonal projection of proprioceptive dorsal root ganglion neurons. *Nat Neurosci.* Oct. 2002;5(10):946-54.

(Continued)

*Primary Examiner* — Christine J Saoud
*Assistant Examiner* — Jon M Lockard
(74) *Attorney, Agent, or Firm* — Wolf, Greenfield & Sacks, P.C.

(57) ABSTRACT

Methods are provided for identifying candidate agents for use in inhibiting expression of certain receptors and ion channels in nociceptors. Also provided are methods for identifying candidates agents for use in inhibiting neurophathic and other types of pain.

24 Claims, 14 Drawing Sheets

OTHER PUBLICATIONS

Jiang X et al., Fate of the mammalian cardiac neural crest. *Development*. Apr. 2000;127(8):1607-16.

Jordt SE et al., Lessons from peppers and peppermint: the molecular logic of thermosensation. *Curr Opin Neurobiol*. Aug. 2003;13(4):487-92.

Lembo PM et al., Proenkephalin A gene products activate a new family of sensory neuron—specific GPCRs. *Nat Neurosci*. Mar. 2002;5(3):201-9.

Levanon D et al., The Runx3 transcription factor regulates development and survival of TrkC dorsal root ganglia neurons. *EMBO J*. Jul. 1, 2002;21(13):3454-63.

Lewin GR et al., A plethora of painful molecules. *Curr Opin Neurobiol*. Aug. 2004;14(4):443-9.

Molliver DC et al., IB4-binding DRG neurons switch from NGF to GDNF dependence in early postnatal life. *Neuron*. Oct. 1997;19(4):849-61.

Snider WD et al., Tackling pain at the source: new ideas about nociceptors. *Neuron*. Apr. 1998;20(4):629-32.

Theriault FM et al., AML1/Runx1 is important for the development of hindbrain cholinergic branchiovisceral motor neurons and selected cranial sensory neurons. *Proc Natl Acad Sci U S A*. Jul. 13, 2004;101(28):10343-8. Epub Jul. 6, 2004.

Wang Q et al., Disruption of the Cbfa2 gene causes necrosis and hemorrhaging in the central nervous system and blocks definitive hematopoiesis. *Proc Natl Acad Sci U S A*. Apr. 16, 1996;93(8):3444-9.

Wolf-Watz M et al., Chloride binding by the AML1/Runx1 transcription factor studied by NMR. *FEBS Lett*. Jan. 12, 2001;488(1-2):81-4.

Wood JN, Recent advances in understanding molecular mechanisms of primary afferent activation. *Gut*. Mar. 2004;53 Suppl 2:ii9-12.

Woolf CJ, Dissecting out mechanisms responsible for peripheral neuropathic pain: implications for diagnosis and therapy. *Life Sci*. Apr. 9, 2004;74(21):2605-10.

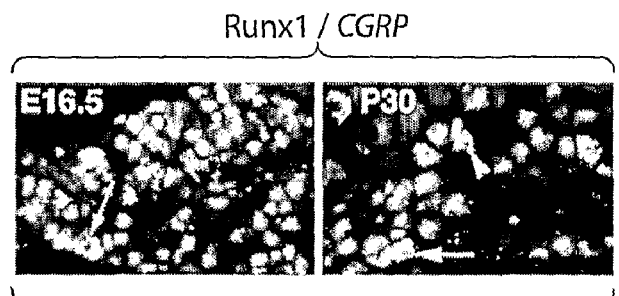
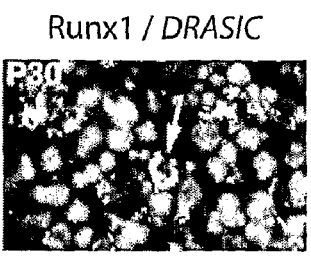
Fig. 5A       Fig. 5B
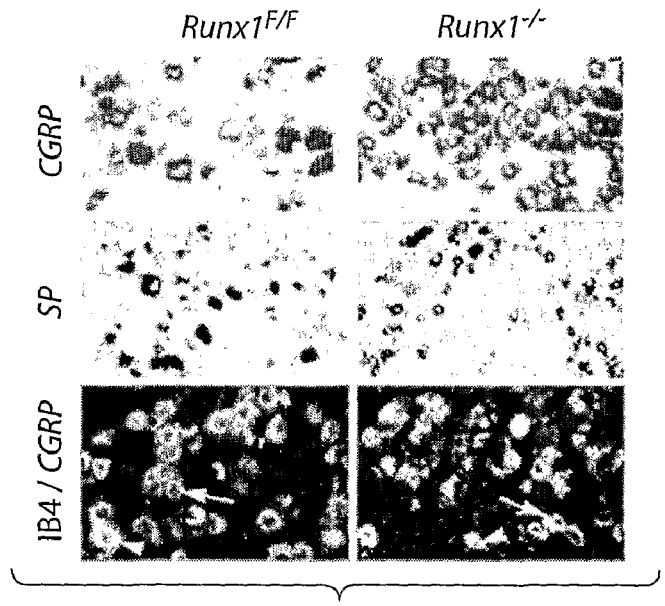
Fig. 5C
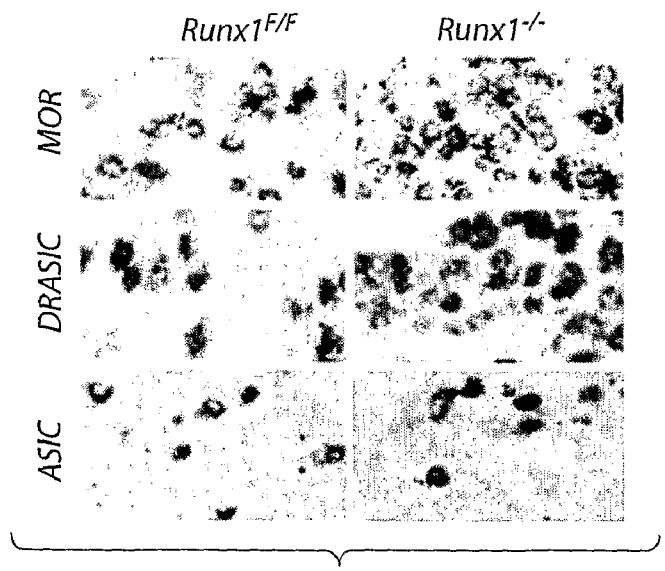
Fig. 5D

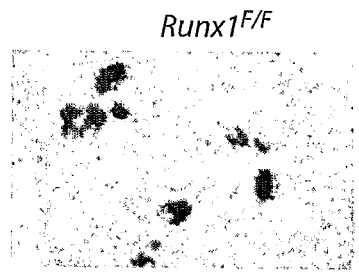
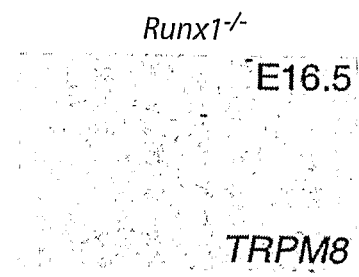
Fig. 6A Fig. 6B
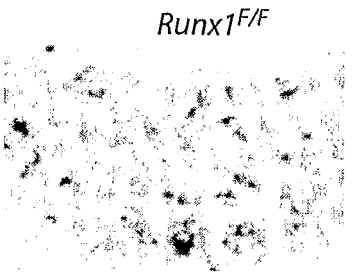
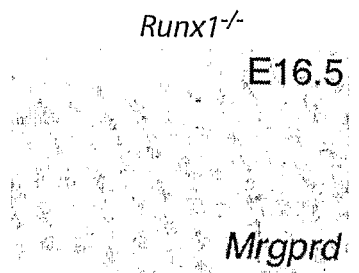
Fig. 6C Fig. 6D
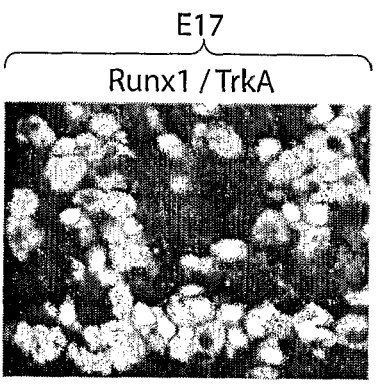
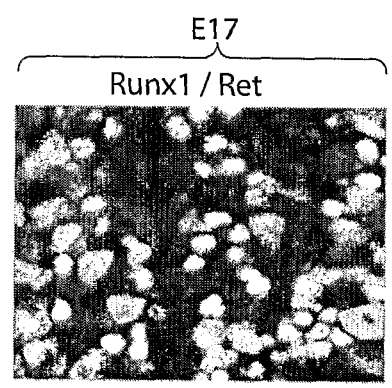
Fig. 6E Fig. 6F
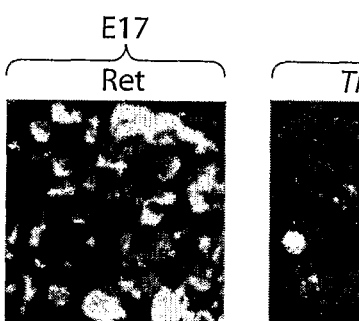
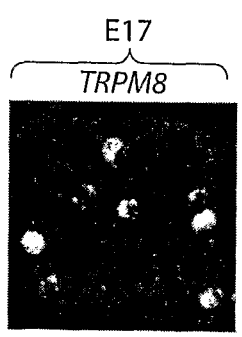
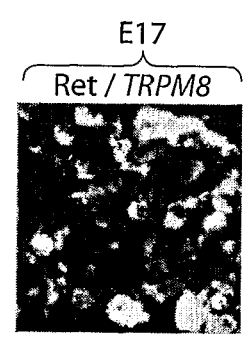
Fig. 6G Fig. 6H Fig. 6I

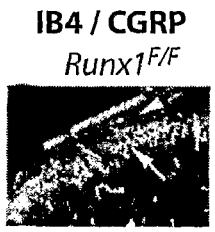
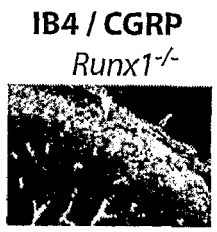
IB4 / CGRP  
*Runx1$^{F/F}$*     *Runx1$^{-/-}$*
Fig. 7A     Fig. 7B
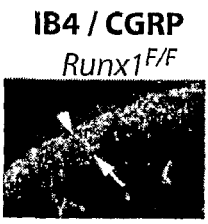
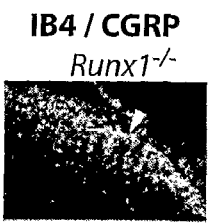
IB4 / CGRP  
*Runx1$^{F/F}$*     *Runx1$^{-/-}$*
Fig. 7C     Fig. 7D
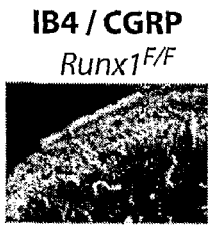
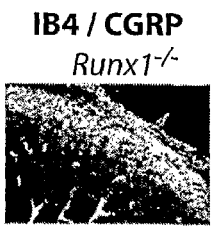
IB4 / CGRP  
*Runx1$^{F/F}$*     *Runx1$^{-/-}$*
Fig. 7E     Fig. 7F
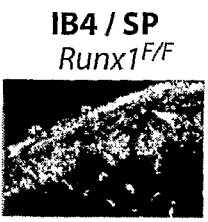
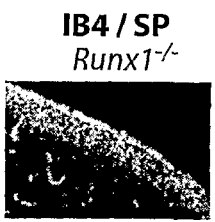
IB4 / SP  
*Runx1$^{F/F}$*     *Runx1$^{-/-}$*
Fig. 7G     Fig. 7H
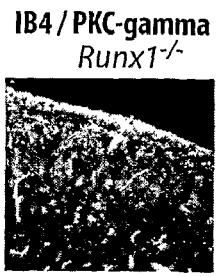
IB4 / PKC-gamma  
*Runx1$^{F/F}$*     *Runx1$^{-/-}$*
Fig. 7I     Fig. 7J

METHODS TO IDENTIFY INHIBITORS OF RUNX1-MEDIATED EXPRESSION OF NOCICEPTIVE RECEPTORS AND ION CHANNELS

FIELD OF THE INVENTION

Sensory neurons enable animals to respond to environmental stimuli, and their diversification into distinct functional subclasses expands perceptual and behavioral repertoires. Nociceptors are a subgroup of primary sensory neurons with cell bodies in the dorsal root and trigeminal ganglia specialized to respond only to noxious/painful stimuli. They serve this function by virtue of the expression of diverse high threshold ion channels and G-protein coupled receptors (GPCRs) that transduce intense mechanical, thermal, or chemical stimuli into electrical activity. Snider W D et al. (1998) *Neuron* 20:629-32; Hunt S P et al. (2001) *Nat Rev Neurosci* 2:83-91; Dong X et al. (2001) *Cell* 106:619-32; Lembo P M et al. (2002) *Nat Neurosci* 5:201-9; Jordt S E et al. (2003) *Curr Opin Neurobiol* 13:487-92; Wood J N (2004) *Gut* 53 Suppl 2, ii9-12; Lewin G R et al. (2004) *Curr Opin Neurobiol* 14:443-9. However, the molecular mechanisms that regulate diverse nociceptor transduction phenotypes remain essentially unknown.

SUMMARY OF THE INVENTION

In mammals, the first step in the perception of pain is the transduction of noxious stimuli by specialized ion channels and receptors expressed by nociceptive sensory neurons. Prior to the invention the mechanisms that regulate the expression of these nociceptive ion channels and receptors were not defined, and, accordingly, it has been unclear whether specific nociceptive transduction phenotypes of distinct nociceptive neurons are allocated in a coordinate or independent fashion.

The present invention is based in part on the discovery by the inventor that the Runt domain transcription factor Runx1 is expressed by a major subset of nociceptors and is required for the expression of many ion channels and receptors—TRP class thermal receptors, $Na^+$ and ATP-gated channels and Mrgpr/SNSR class G-protein coupled receptors—implicated in nociceptive processing. It has also been discovered according to the present invention that Runx1-deficient mice exhibit selective defects in thermal, neuropathic, and inflammatory pain. The invention thus is also based in part on the discovery by the inventor of Runx1-dependent coordinate transcriptional regulation of divergent nociceptor transduction phenotypes. In particular, the invention relates to a novel therapeutic strategy for pain treatment by targeting a Runx1-mediated core transcriptional control program that is required for the expression of a large cohort of nociceptive receptors and channels. Such strategy is likely more effective than conventional strategies of developing drugs based on targeting individual channels or receptors involved in nocieptive processing.

The invention in general provides methods useful for the identification of agents that can be used to regulate expression and function of certain nociceptors and be used for intervention in pain management, including neuropathic pain, inflammatory pain, and other types of pain (such as cancer pain) that have inflammatory and neuropathic pain components. More particularly, the methods of the invention are useful for identifying agents which can be used to regulate expression and function of nociceptors whose expression is affected by Runx1.

In one aspect the invention provides a method for identifying a candidate inhibitor of Runx1-mediated expression of a nociceptive receptor or ion channel. The method according to this aspect of the invention includes the steps of contacting a test cell that expresses Runx1 and comprises a nucleic acid encoding a nociceptive receptor or ion channel operatively linked to a Runx1-sensitive promoter, with a test agent and measuring a test amount of expression of the nociceptive receptor or ion channel; comparing the test amount of expression of the nociceptive receptor or ion channel to a control amount of expression of the nociceptive receptor or ion channel measured in a control cell that expresses Runx1 and comprises the nucleic acid encoding the nociceptive receptor or ion channel operatively linked to the Runx1-sensitive promoter, wherein the control cell is not contacted with the test agent; and identifying the test agent as a candidate inhibitor of Runx1-mediated expression of a nociceptive receptor or ion channel when the control amount of expression is greater than the test amount of expression.

In one aspect the invention provides a method for identifying a candidate inhibitor of Runx1-mediated expression of a nociceptive receptor or ion channel. The method according to this aspect of the invention includes the steps of contacting a test cell that expresses Runx1 and comprises a nucleic acid encoding a reporter operatively linked to a Runx1-sensitive promoter, with a test agent and measuring a test amount of expression of the reporter; comparing the test amount of expression of the reporter to a control amount of expression of the reporter measured in a control cell that expresses Runx1 and comprises the nucleic acid encoding the reporter operatively linked to the Runx1-sensitive promoter; and identifying the test agent as a candidate inhibitor of Runx1-mediated expression of a nociceptive receptor or ion channel when the control amount of expression is greater than the test amount of expression.

In one aspect the invention provides a method for identifying a candidate agent for use in inhibiting neuropathic pain and other types of pain. The method according to this aspect of the invention includes the steps of contacting a test cell that expresses Runx1 and comprises a nucleic acid encoding a nociceptive receptor or ion channel operatively linked to a Runx1-sensitive promoter, with a test agent and measuring a test amount of expression of the nociceptive receptor or ion channel; comparing the test amount of expression of the nociceptive receptor or ion channel to a control amount of expression of the nociceptive receptor or ion channel measured in a control cell that expresses Runx1 and comprises the nucleic acid encoding the nociceptive receptor or ion channel operatively linked to the Runx1-sensitive promoter, wherein the control cell is not contacted with the test agent; and identifying the test agent as a candidate agent for use in inhibiting neuropathic pain and other types of pain when the control amount of expression is greater than the test amount of expression.

In one aspect the invention provides a method for identifying a compound for use in inhibiting neuropathic pain and other types of pain. The method according to this aspect of the invention includes the steps of measuring a test amount of binding between Runx1 and a Runx1-sensitive promoter for a nociceptor in presence of a test compound; comparing the test amount of binding to a control amount of binding between Runx1 and the promoter for the nociceptor in absence of the test compound; and identifying the test compound as a compound for use in inhibiting neuropathic pain and other types of pain when the test amount of binding is less than the control amount of binding.

In one aspect the invention provides a method for identifying a candidate compound for use in inhibiting neuropathic pain and other types of pain. The method according to this aspect of the invention includes the steps of contacting a test cell that expresses Runx1 with a test agent and measuring a test amount of Runx1 protein or Runx1 messenger RNA; comparing the test amount of Runx1 protein or messenger RNA to a control amount of Runx1 protein or Runx1 messenger RNA measured in absence of the test compound; and identifying the test compound as a candidate compound for use in inhibiting neuropathic pain and other types of pain when the test amount of Runx1 protein or Runx1 messenger RNA is less than the control amount.

In one embodiment the nucleic acid encoding the nociceptive receptor or ion channel operatively linked to the Runx1-sensitive promoter is a gene for the nociceptive receptor or ion channel, wherein the gene includes an intrinsic promoter.

In one embodiment the nucleic acid encoding the nociceptive receptor or ion channel operatively linked to the Runx1-sensitive promoter encodes a nociceptive receptor or ion channel chosen from TRPC3, TRPM8, TRPA1, Mrgprd, P2X3, Nav1.9/SNS2, and any combination thereof.

In one embodiment the nociceptive receptor or ion channel is TRPC3.

In one embodiment the test cell includes a Runx1 expression vector.

In one embodiment the control cell includes a Runx1 expression vector.

In one embodiment the test amount of expression and the control amount of expression are corresponding amounts of transcript for the nociceptive receptor or ion channel.

In one embodiment the test amount of expression and the control amount of expression are corresponding amounts of protein for the nociceptive receptor or ion channel.

In one embodiment the nucleic acid encoding the nociceptive receptor or ion channel operatively linked to the Runx1-sensitive promoter is part of an expression vector.

In one embodiment the control cell is a dorsal root ganglion cell derived from a Runx1$^{-/-}$ (Runx1$^{F/F}$; Wnt1-Cre) mouse.

In one embodiment the reporter expression is measured as fluorescence emitted by the reporter.

In one embodiment the test compound is selected from the group consisting of small molecules, peptides, nucleic acids, and any combination thereof.

In one embodiment the test compound is a small molecule.

In one embodiment the test compound is a nucleic acid.

In one embodiment the test compound inhibits expression of Runx1.

In one embodiment the reporter is green fluorescent protein.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

mice, double stained by in situ hybridization for TrkA (bright, originally green and/or yellow) and for IB4 binding (less bright, originally red). In wild-type DRG, IB4+ cells do not coexpress TrkA.

Figure 3A:
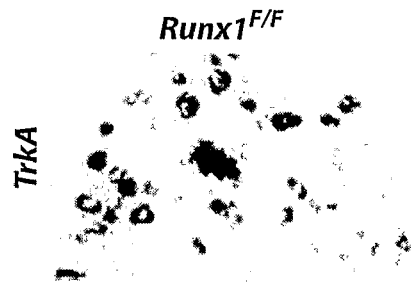
FIGS. 3A and 3B are photomicrographs of transverse sections through DRGs of adult wild-type (A) and Runx1$^{-/-}$ (B) mice, stained by in situ hybridization for TrkA.
Figure 3B:
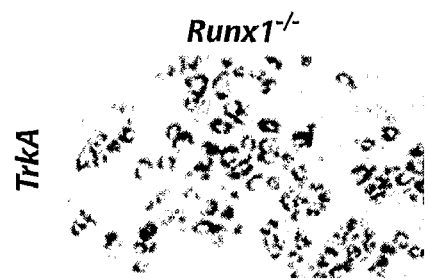
Figure 3C:
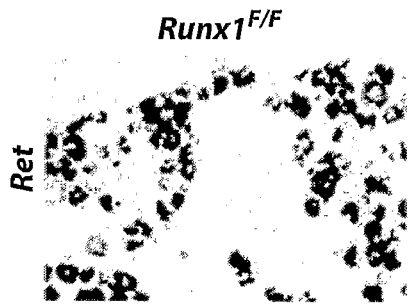
FIGS. 3C and 3D are photomicrographs of transverse sections through DRGs of adult wild-type (C) and Runx1$^{-/-}$ (D) mice, stained by in situ hybridization for Ret.
Figure 3D:
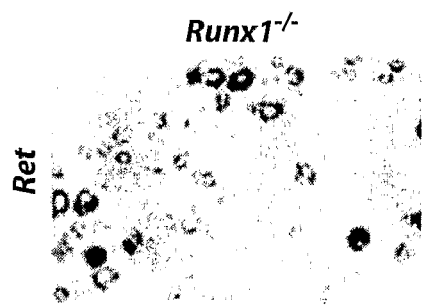
Figure 3E:
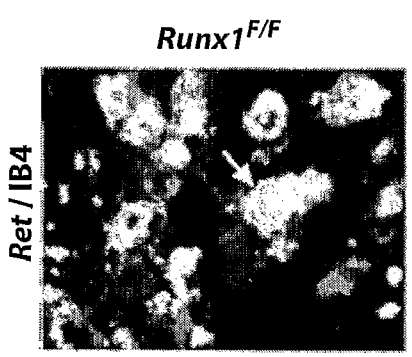
FIGS. 3E and 3F are photomicrographs of transverse sections through DRGs of adult wild-type (E) and Runx1$^{-/-}$ (F) mice, double stained by in situ hybridization for Ret (less bright, originally red) and IB4 binding (bright, originally green).
Figure 3F:
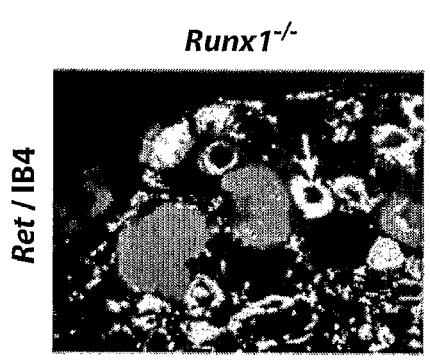
Figure 3G:
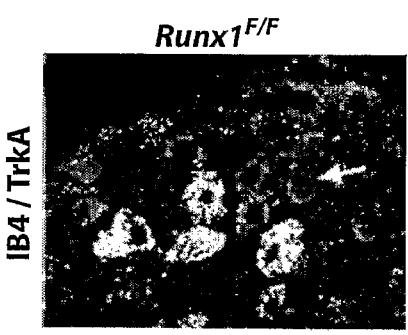
FIGS. 3G and 3H are photomicrographs of transverse sections through DRGs of adult wild-type (G) and Runx1$^{-/-}$ (H)
Figure 3H:
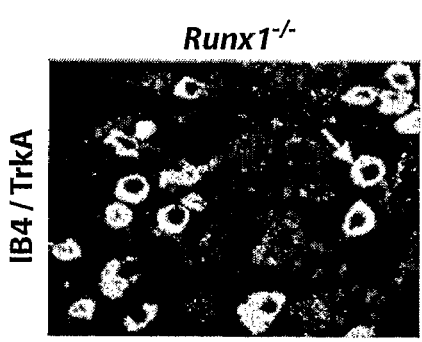
Figure 3I:
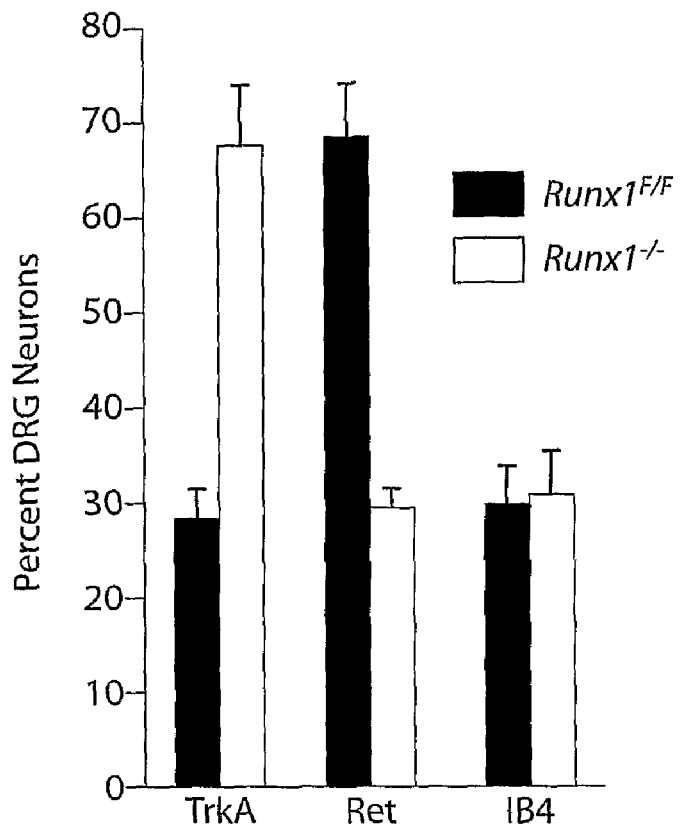

FIG. 3I is a bar graph depicting percentages of DRG neurons expressing TrkA, Ret, and IB4 in wild-type mice (Runx1$^{F/F}$, filled bars) and Runx1$^{-/-}$ mice (unfilled bars).

Figure 3J:
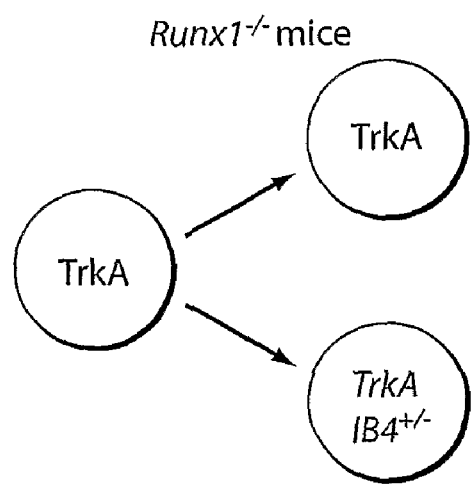

FIG. 3J is a schematic diagram depicting transformation of prospective Ret+ into TrkA+ nociceptors in Runx1$^{-/-}$ mice.

FIG. 4 is an array of paired photomicrographs of sections through adult wild-type and Runx1$^{-/-}$ DRG, with in situ hybridization performed with indicated probes for (4A:) TRPA1, TRPM8, TRPC3, TRPV1, TRPV2; (4B:) Mrgprb4, Mrgprb5, Mrgprad; (C:) Nav1.9; and (D:) P2X3. Arrows point out selective reduction of high-level expression of TRPV1, TRPV2 and Nav1.9 in Runx1$^{-/-}$ mice. Arrowheads point out intermediate expression of TRPV1, TRPV2 and Nav1.9 in Runx1$^{-/-}$ mice. FIG. 4E is a panel of four photomicrographic images of sections of P30 wild-type DRG double labeled for Runx1 protein (bright, originally green) and the indicated probes (less bright, originally red).

FIG. 5A is a pair of photomicrographic images depicting double labeling of Runx1 protein (bright, originally green) and Calcitonin Gene Related Peptide (CGRP) (less bright, originally red) in E16.5 and P30 DRG sections from wild-type Runx1$^{F/F}$ mice. Runx1+ neurons do not express CGRP at E16.5 (arrows) but some CGRP+ neurons express a low level of Runx1 at P30 (arrowhead).

FIG. 5B is a photomicrographic image depicting double labeling of Runx1 protein (bright, originally green) and DRASIC (less bright, originally red) in P30 DRG sections from wild-type Runx1$^{F/F}$ mice. Runx1+ neurons do not express DRASIC at P30 (arrow).

FIG. 5C is a panel of six photomicrographic images depicting expression of CGRP, Substance P (SP), and combined IB4 and CGRP in sections of adult wild-type (Runx1$^{F/F}$) (left) and Runx1$^{-/-}$ (right) DRG. Arrows, CGRP+; arrowheads, CGRP−.

FIG. 5D is a panel of six photomicrographic images depicting expression of mu-class opioid receptor (MOR), DRASIC, and ASIC in sections of adult wild-type (Runx1$^{F/F}$) (left) and Runx1$^{-/-}$ (right) DRG.

Figure 5E:
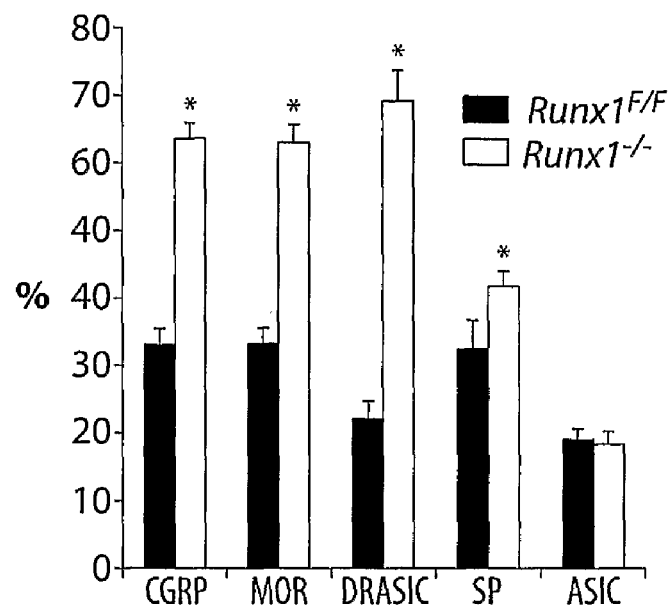

FIG. 5E is a bar graph depicting the average (±SEM) percentages of DRG neurons expressing the indicated markers in adult wild-type (Runx1$^{F/F}$) (filled bars) and Runx1$^{-/-}$ (open bars) mice. * t test P<0.001.

Figure 5F:
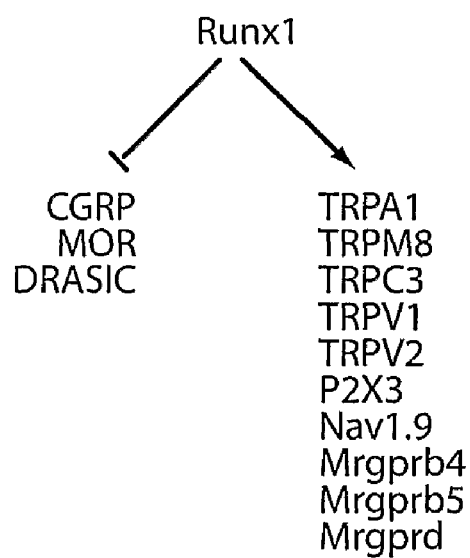

FIG. 5F is a schematic representation showing how Runx1 activates and suppresses two separate groups of neuropeptides, ion channels, and sensory receptors.

FIG. 6A-6D are photomicrographic images depicting in situ hybridization of TRPM8 (A and B) and Mrgprd (C and D) in E16.5 sections of wild-type Runx1$^{F/F}$ (A and C) and Runx1$^{-/-}$ (B and D) DRG.

FIG. 6E is a photomicrographic image depicting double immunoassaying of Runx1 protein (bright, originally green) with TrkA protein (less bright, originally red) in E17 wild-type DRG.

FIG. 6F is a photomicrographic image depicting double immunostaining of so Runx1 protein (bright, originally green) with Ret protein (less bright, originally red) in E17 wild-type DRG.

FIG. 6G-I are a panel of three photomicrographic images depicting double staining of TRPM8 mRNA (bright, originally green) and Ret protein (less bright, originally red) in E17 wild-type DRG.

FIGS. 7A and 7B are a pair of photomicrographic images depicting staining for IB4 (originally green) in P30 dorsal horn sections from wild-type (Runx1$^{F/F}$) mice (left) and Runx1$^{-/-}$ mice (right). Arrowheads, superficial lamina; arrow, deep lamina.

FIGS. 7C and 7D are a pair of photomicrographic images depicting staining for CGRP (originally red) in P30 dorsal horn sections from wild-type (Runx1$^{F/F}$) mice (left) and Runx1$^{-/-}$ mice (right). Arrowheads, superficial lamina; arrow, deep lamina.

FIGS. 7E and 7F are a pair of merged photomicrographic images of FIGS. 7A and 7C and of FIGS. 7B and 7D, respectively.

FIGS. 7G and 7H are a pair of photomicrographic images depicting double staining of IB4 (originally green) and Substance P (SP; originally red) in P30 dorsal horn sections from wild-type (Runx1$^{F/F}$) mice (left) and Runx1$^{-/-}$ mice (right). Arrowhead, superficial lamina.

FIGS. 7I and 7J are a pair of photomicrographic images depicting double staining of IB4 (originally green) and protein kinase C-gamma (PKC-gamma; originally red) in P30 dorsal horn sections from wild-type (Runx1$^{F/F}$) mice (left) and Runx1$^{-/-}$ mice (right). Arrows, deep lamina.

Figure 7K:
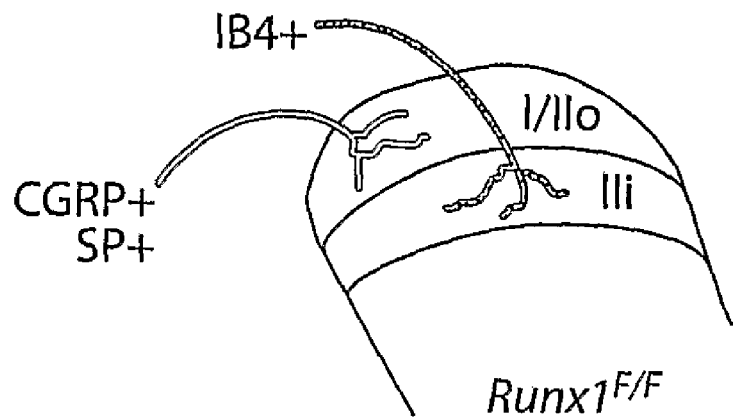

FIG. 7K is a schematic drawing depicting deep lamina-specific innervation of IB4 afferents in wild-type (Runx1$^{F/F}$) dorsal horn.

Figure 7L:
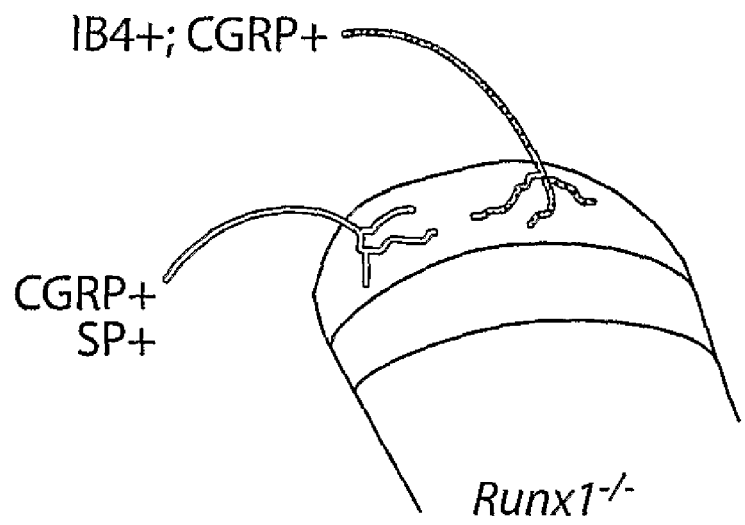

FIG. 7L is a schematic drawing depicting more superficial lamina-specific innervation of IB4+ afferents in Runx1$^{-/-}$ dorsal horn.

Figure 8A:
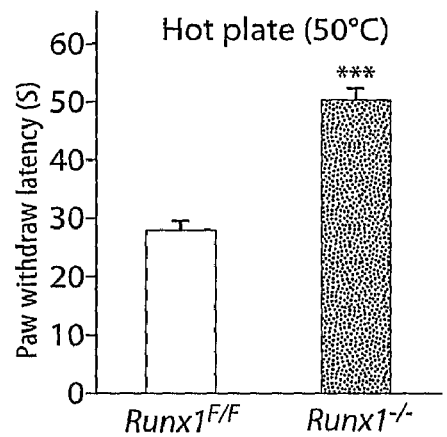
Figure 8B:
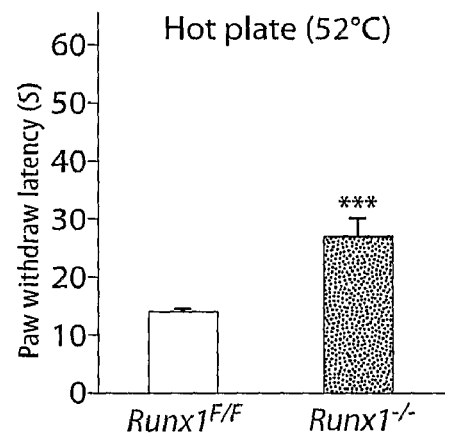

FIGS. 8A and 8B are bar graphs depicting behavioral sensitivity of control Runx1$^{F/F}$ mice (open bars) and Runx1$^{-/-}$ mice (hatched bars) to heat at the indicated temperatures. *** P<0.001.

Figure 8C:
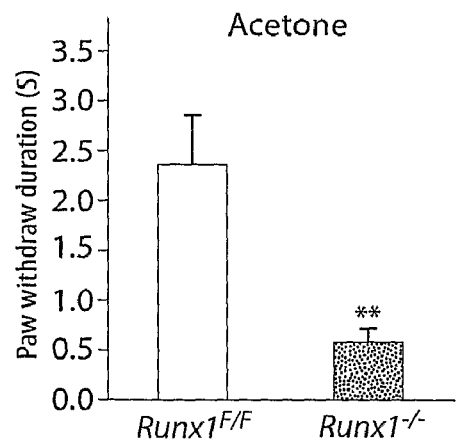

FIG. 8C is a bar graph depicting behavioral sensitivity of control Runx1$^{F/F}$ mice (open bars) and Runx1$^{-/-}$ mice (hatched bars) to cold. ** P<0.01.

Figure 8D:
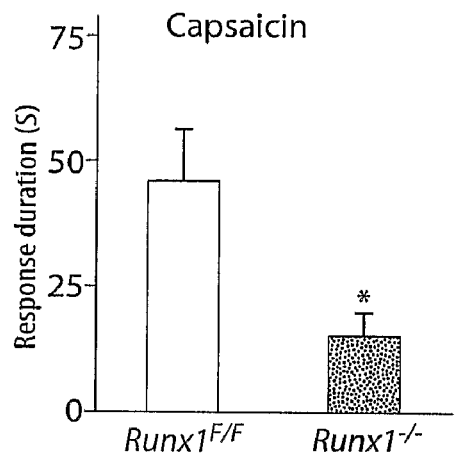

FIG. 8D is a bar graph depicting behavioral sensitivity of control Runx1$^{F/F}$ mice (open bars) and Runx1$^{-/-}$ mice (hatched bars) to capsaicin-induced chemical pain. * P<0.05.

Figure 8E:
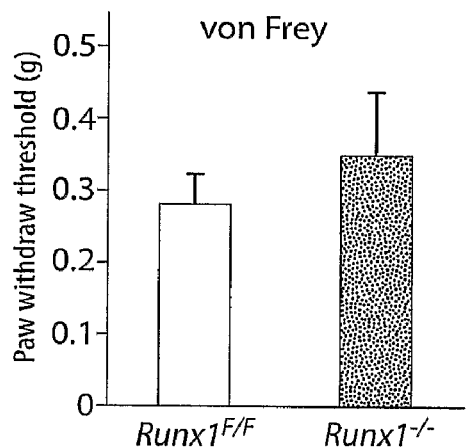
Figure 8F:
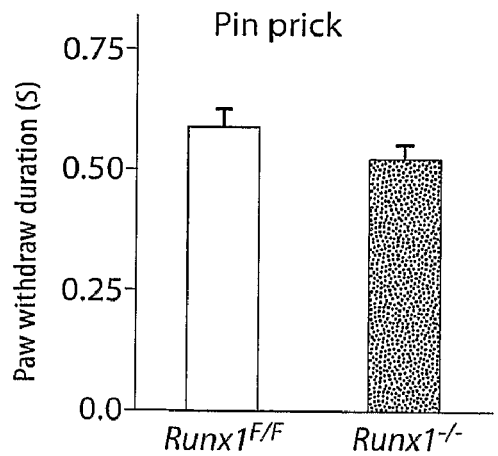

FIGS. 8E and 8F are bar graphs depicting behavioral sensitivity of control Runx1$^{F/F}$ mice (open bars) and Runx1$^{-/-}$ mice (hatched bars) to mechanical pain induced with von Frey hair (E) or pin prick (F).

Figure 8G:
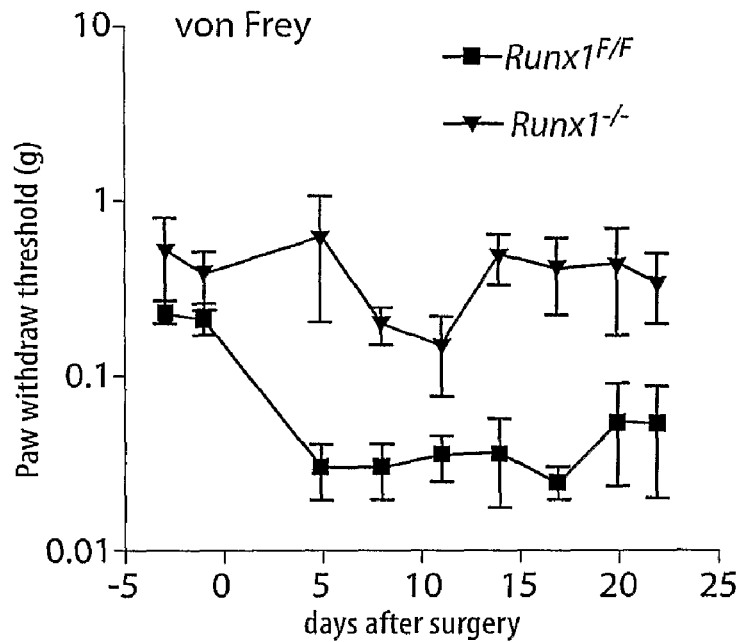

FIG. 8G is a graph depicting mechanical allodynia in control Runx1$^{F/F}$ mice (square symbols) and Runx1$^{-/-}$ mice (triangle symbols) in the spared nerve injury model of neuropathic pain.

Figure 8H:
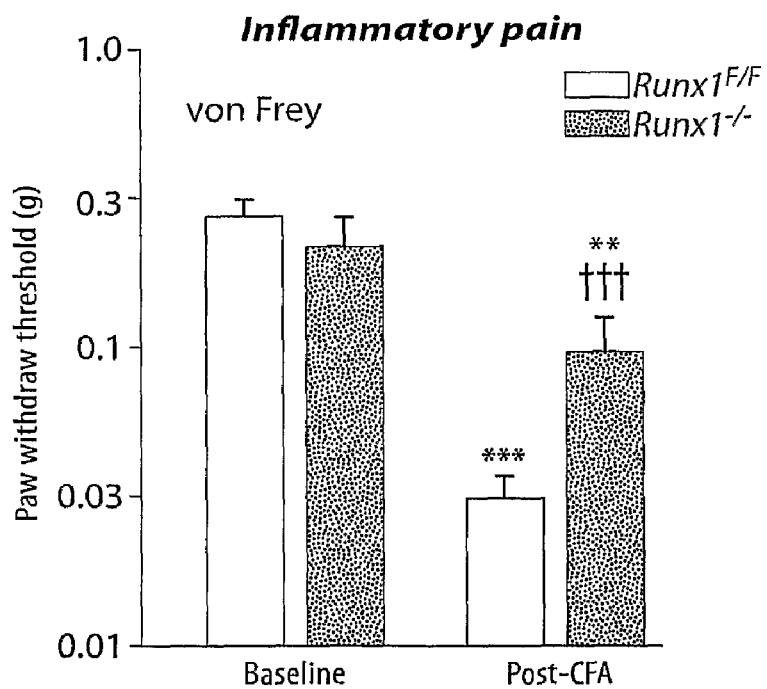

FIG. 8H is a bar graph depicting behavioral sensitivity of control Runx1$^{F/F}$ mice (open bars) and Runx1$^{-/-}$ mice (hatched bars) to inflammatory pain.  P<0.01 and * P<0.001 compared to baseline; ††† P<0.001 compared to control Runx1$^{F/F}$ mice. CFA, complete Freund's adjuvant.

DETAILED DESCRIPTION OF THE INVENTION

Runx1 (runt-related transcription factor 1) is a mammalian transcription factor that is encoded by Runx1, a gene related to the runt gene in *Drosophila melanogaster*. In *Drosophila* the runt gene has been reported to be involved in several developmental pathways, including segmentation, sex determination, and neurogenesis. In mammals Runx1 encodes the DNA-binding subunit of the heterodimeric core-binding factor (CBF). CBF consists of a DNA-binding alpha (α) subunit that contacts DNA directly, and a beta (β) subunit that forms a complex with the cc subunit and enhances CBF affinity for DNA without itself binding to DNA. In mammals CBFα subunits are encoded by at least three distinct genes (Cbfa1, Cbfa2, and Cbfa3), while a single gene (Cbfb) encodes the CBFβ subunit. Chromosomal translocations involving the Cbfa2 gene, also known as Runx1 and as AML1, have been associated with common forms of leukemias and myelodysplasias in humans.

CBF has been reported to bind to 5'-YGYGGT-3' or 5'-PYGPYGGT-3' (P=purine, Y=pyrimidine) sites found in the promoters and enhancers of many genes encoding a diverse set of proteins including cytokines, cell surface differentiation markers, and myeloid-specific proteins. In addition to their expression in hematopoietic cells, transcription factor Runx1 (also known in the literature as AML1, CBFA2, EVI-1, AMLCR1, PEBPα2, PEBP2αB, and AML1-EVI-1) and another Runt class transcription factor, Runx3/PEBP2βC/AML2 (de Bruijn MY et al. (2004) *Oncogene* 23:4238-48), have been reported to be expressed by cutaneous and proprioceptive sensory neurons, respectively, in the dorsal root ganglia (DRG), and Runx3 has been implicated in the differentiation of proprioceptive sensory neurons. Inoue K et al. (2002) *Nat Neurosci* 5:946-954; Levanon D et al. (2002) *EMBO J* 21:3454-63; Theriault F M et al. (2004) *Proc Natl Acad Sci USA* 101:10343-8.

The cDNA sequences of at least two transcript variants of human Runx1 are known. These include a longer isoform (a), encoding a 480 amino acid transcription factor protein, and a shorter isoform (b), encoding a 453 amino acid transcription factor protein. Nucleotide sequences for these two isoforms are available as GenBank accession numbers NM_001754 and NM_001001890, respectively. A genomic sequence for human Runx1 is available as GenBank accession number AF025841.

At least five isoforms of murine Runx1 have been reported, including isoforms 1 (451 amino acids) and isoform 4 (465 amino acids). Nucleic acid and amino acid sequences for these isoforms are available from GenBank, e.g., D13802 (isoform 1). See also GenBank Q03347. A genomic sequence for murine Runx1 is available as GenBank accession number 193030.

Until now efforts to elucidate further the function of Runx1 through the use of Runx1-deficient mice have been impeded by the fact that such mutations are lethal during development. More specifically, it has been reported that disruption of the Runx1 gene such that its expression product no longer can bind DNA causes necrosis and hemorrhaging in the central nervous system and blocks definitive hematopoiesis during embryogenesis. Wang Q et al. (1996) *Proc Natl Acad Sci USA* 93:3444-9.

Figure 2A:
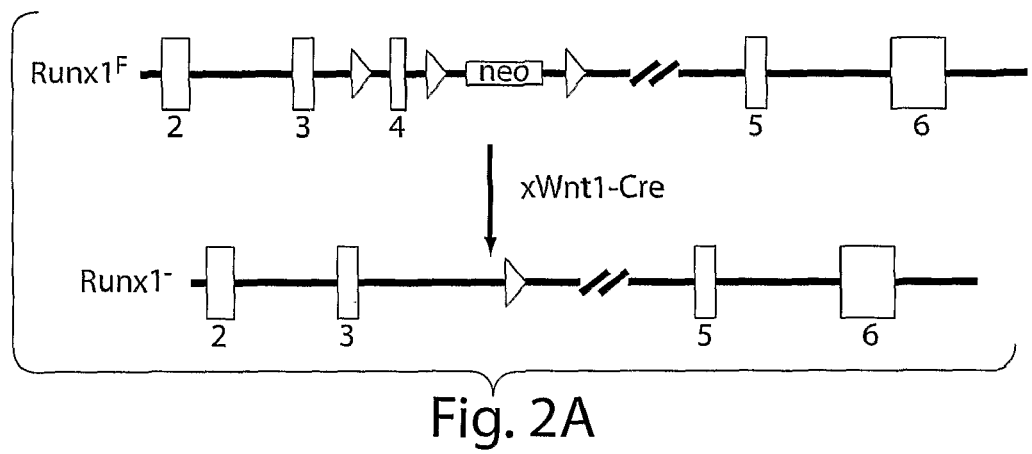
FIG. 2A is a schematic depiction of the conditional allele Runx1$^F$ (top) and the result of crossing the conditional allele Runx1$^F$ with Wnt1-Cre (bottom), generating Runx1$^{-/-}$ mice lacking Runx1 expression in neural crest cells. Numbered vertical bars represent exons. Exon 4 is flanked by loxP sequences (triangles), as is a neo cassette in the intron between exons 4 and 5.
Figure 2B:
FIG. 2B is a pair of photomicrographic images showing Runx1 expression in sections of adult DRG taken from wild-type (Runx1$^{F/F}$, left) and Runx1$^{-/-}$ (right) mice.
Figure 2C:
FIG. 2C is a pair of photomicrographic images showing pan-neuronal marker SCG10 expression in sections of adult DRG taken from wild-type (Runx1$^{F/F}$, left) and Runx1$^{-/-}$ (right) mice.
Figure 2D:
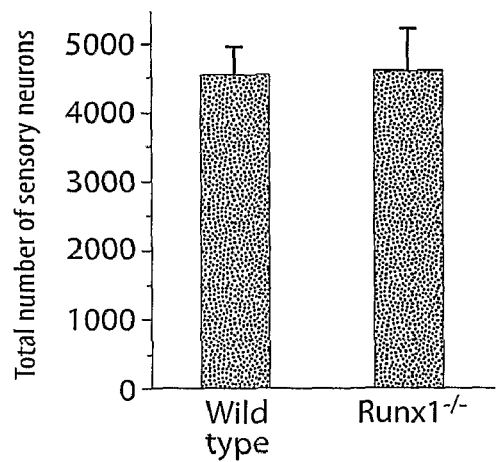
FIG. 2D is a bar graph depicting the total number of SCG10$^+$ neurons in fifth lumbar DRG in wild-type (Runx1$^{F/F}$) and Runx1$^{-/-}$ mice.

As disclosed in greater detail below in Example 1, in order to examine the influence of Runx1 on the differentiation of nociceptive sensory neurons, mice carrying a loxP-based conditional Runx1 allele (referred to here as Runx1$^F$; FIG. 2A) were crossed with a Wnt1-Cre mouse strain that directs Cre expression in neural crest progenitors of DRG neurons. Jiang X et al. (2000) *Development* 127:1607-16. In Runx1$^{-/-}$ mice so derived there is no detectable expression of Runx1 in DRG neurons, suggesting complete penetrance of Cre-mediated recombination. Runx1$^{-/-}$ mice are viable and fertile with no overt abnormalities. Moreover, DRG neuronal numbers are similar in Runx1$^{-/-}$ and control Runx1$^{F/F}$ mice, indicating that Runx1 is not required for the genesis or survival of DRG neurons.

Figure 1A:
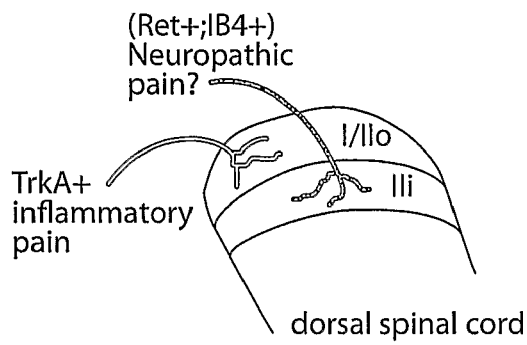
FIG. 1A is a schematic illustration depicting projections of different classes of nociceptors into different laminae of spinal cord of wild-type mice, with levels I/IIo being most superficial. Ret+ nociceptors, which are involved in neuropathic pain, project to deeper laminae.
Figure 1B:
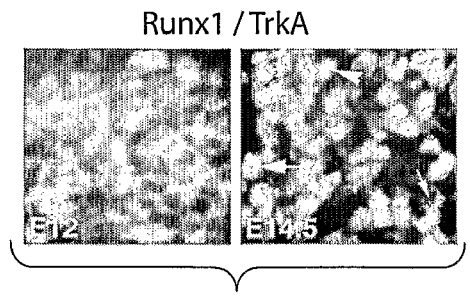
FIG. 1B is a pair of photomicrographs depicting a transverse section through embryonic (E12 and E14.5) dorsal root ganglion (DRG) immunostained for Runx1 (bright, originally green) and TrkA (less bright, originally red). All Runx1$^+$ cells at this stage coexpress TrkA but not Ret, whereas a small subset of TrkA$^+$ neurons lacks Runx1 expression.
Figure 1C:
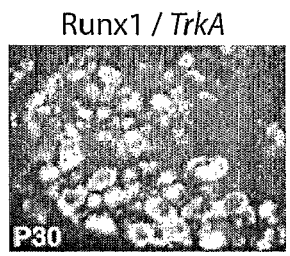
FIG. 1C is a photomicrograph depicting a transverse section through a one-month old (P30) DRG double stained for Runx1 protein (bright, originally green) and TrkA mRNA (less bright, originally red).
Figure 1D:
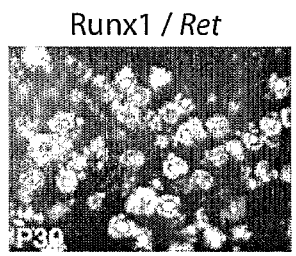
FIG. 1D is a photomicrograph depicting a transverse section through a one-month old (P30) DRG double stained for Runx1 protein (bright, originally green) and Ret mRNA (less bright, originally red).
Figure 1E:
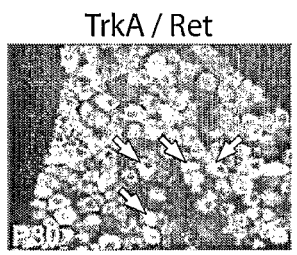
FIG. 1E is a photomicrograph depicting a transverse section through a one-month old (P30) DRG double stained for Trk, mRNA and Ret mRNA. DRG neurons expressing TrkA alone appear bright, originally red, those expressing Ret alone appear brighter, originally green, and those expressing both TrkA and Ret appear brightest, originally partially yellow (arrows).
Figure 1F:
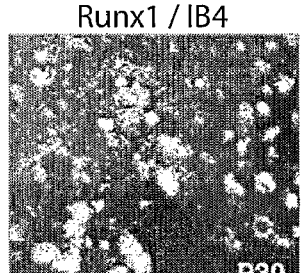
FIG. 1F is a photomicrograph depicting a transverse section through a one-month old (P30) DRG double stained for Runx1 protein (bright, originally green) and cell surface lectin IB4 (less bright, originally red). IB4 is a marker for a subset of Ret$^+$ neurons.
Figure 1G:
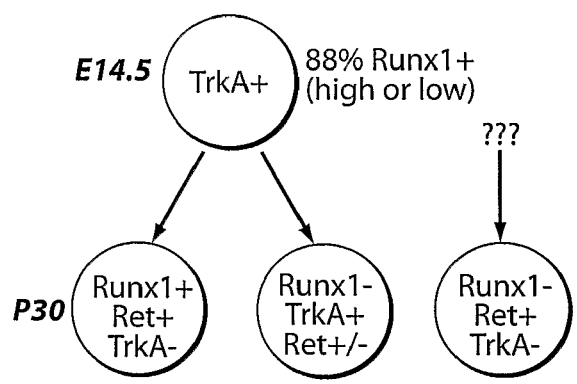
FIG. 1G is a schematic diagram indicating that Runx1 is expressed broadly in E14.5 TrkA$^+$ neurons and that its expression persists in a subset of Ret$^+$ neurons but extinguishes in TrkA$^+$ neurons. TrkA expression also extinguishes in adult Runx1$^+$; Ret$^+$ neurons. The origin, identity and function of Runx1$^-$; TrkA$^-$; Ret$^+$ cells remain obscure.

Soon after their generation, most embryonic nociceptive neurons express the high affinity nerve growth factor (NGF) receptor TrkA, but later in development about half of these neurons extinguish TrkA and begin to express Ret, a glial-derived growth factor (GDNF) receptor (Snider W D et al. (1998) *Neuron* 20:629-32; Molliver D C et al. (1997) *Neuron* 19:849-61) (FIG. 1). In wild-type mice, Runx1 expression is first detected in DRG neurons at embryonic day (E) 11.5, after the onset of TrkA expression, and until E14.5, Runx1 expression is confined to TrkA$^+$ neurons (FIG. 1B), with ~90% of TrkA$^+$ neurons expressing Runx1 (FIG. 1B, FIG. 1G). By postnatal day (P) 6.5, extinction of TrkA expression from some Runx1$^+$ neurons begins, and by P30 Runx1$^+$ neurons only rarely co-express TrkA (FIG. 1C) and most co-express Ret instead (FIG. 1D). Thus, in wild-type mice, the persistence of Runx1 expression is associated with sensory neurons that undergo the developmental transition from a TrkA$^+$ to a Ret$^+$ nociceptor phenotype (FIG. 1G).

The invention relates in certain aspects to methods of identifying a candidate inhibitor of Runx1-mediated expression of a nociceptive receptor or ion channel. As disclosed herein, it has been discovered according to the invention that Runx1 is involved in the coordinate expression of a host of nociceptors of certain classes. These nociceptors relate especially to those involved in sensing painful thermal and mechanical stimuli.

As used herein, the term "nociceptor" refers to any of a subgroup of primary sensory neurons with cell bodies in the dorsal root and trigeminal ganglia specialized to respond only to noxious stimuli. Nociceptors serve this function by virtue of their expression of diverse high threshold ion channels and G-protein coupled receptors (GPCRs) that transduce intense mechanical, thermal, or chemical stimuli into electrical activity.

As used herein, the term "nociceptive receptor or ion channel" refers to any GPCR or high threshold ion channel that is expressed by a nociceptor and is involved in transducing mechanical, thermal, or chemical stimuli into electrical activity. Nociceptive receptors and ion channels specifically can include, but are not limited to, TRPA, TRPM8, TRPC3, TRPV1, TRPV2, P2X3, the Mrg family of GPCRs (encompassing a dozen or more receptors including Mrgpra, Mrgprb, Mrgprc, and Mrgprd family members), and tetrodotoxin-resistant sodium channels such as Nav1.9.

Certain methods of the invention involve contacting a test agent with a cell that expresses Runx1 and includes a nucleic acid encoding a nociceptive receptor or ion channel operatively linked to a Runx1-sensitive promoter.

As used herein, the term "nucleic acid encoding a nociceptive receptor or ion channel" refers to any DNA or RNA molecule that encodes such receptor or ion channel. In one embodiment the nucleic acid is a genomic DNA encoding the nociceptive receptor or ion channel. In one embodiment the nucleic acid is a complementary DNA (cDNA) encoding the nociceptive receptor or ion channel. In either of these embodiments the encoding DNA can be operatively linked to an endogenous or exogenous (heterologous) promoter that is responsive to binding by Runx1. In one embodiment the nucleic acid encoding a nociceptive receptor or ion channel is a gene, including at least a portion of its native or endogenous promoter, that encodes a nociceptive receptor or ion channel.

In one embodiment the nucleic acid encoding a nociceptive receptor or ion channel is naturally expressed by a cell used in a method of the invention. In such embodiment the nucleic acid encoding a nociceptive receptor or ion channel is a gene, including its native or endogenous promoter, that encodes a nociceptive receptor or ion channel. In one embodiment the endogenous promoter is a Runx1-sensitive promoter.

In one embodiment the nucleic acid encoding a nociceptive receptor or ion channel is not naturally expressed by a cell used in a method of the invention. In such embodiment the nucleic acid encoding a nociceptive receptor or ion channel is a nucleic acid that is artificially introduced into the cell, for example by transfection with a suitable expression vector for the receptor or ion channel. The nucleic acid encoding a nociceptive receptor or ion channel in one embodiment is operatively linked to an endogenous or exogenous (heterologous) promoter. In one embodiment the endogenous promoter is a Runx1-sensitive promoter. In one embodiment the exogenous (heterologous) promoter is a Runx1-sensitive promoter.

As used herein, the term "Runx1-sensitive promoter" refers to a nucleic acid including a promoter of gene transcription, wherein the promoter includes a sequence specifically bound by a Runt domain of Runx1 transcription factor. Promoters generally include 5' untranscribed, untranslated DNA sequence found upstream of (5' to) the coding sequence (open reading frame) of a gene. A promoter typically spans hundreds of nucleotides but can be longer or shorter. Promoters can include one or more transcription factor response elements, which are DNA sequences recognized and bound by transcription factors. The sequence bound by the Runt domain typically will include a DNA sequence 5'-YGYGGT-3' or 5'-PYGPYGGT-3', where G=guanine, P=purine, T=thymine, and Y=pyrimidine.

In certain embodiments the Runx1-sensitive promoter is a promoter for a gene encoding a nociceptive receptor or ion channel. Nociceptive receptors and ion channels include those disclosed above, and they can include those from human and other mammalian species. Nucleotide sequences for genes encoding such proteins are available from public databases such as GenBank. For example, human and murine cDNA sequences for TRPC3 are available as GenBank accession numbers NM_003305 and NM_019510, respectively. Human and murine cDNA sequences for TRPM8 are available as GenBank accession numbers NM_024080 and NM_134252, respectively. Human and murine cDNA sequences for TRPV1 are available as GenBank accession numbers NM_080706 and NM_001001445, respectively, and a genomic sequence for murine TRPV1 is available as GenBank accession number AL663116. Human and murine cDNA sequences for TRPV2 are available as GenBank accession numbers NM_016113 and NM_011706, respectively, and a genomic sequence for human TRPV2 is available as GenBank accession number A94121. Human and murine cDNA sequences for P2X3 are available as GenBank accession numbers NM_002559 and NM_145526, respectively. Human and murine cDNA sequences for Mrgprd are available as GenBank accession numbers NM_198923 and NM_203490, respectively, and genomic sequences for murine Mrgprd are available as GenBank accession numbers AB 154412 and AY042209. Genomic and cDNA sequences for human Nav1.9 are available as GenBank accession numbers AF126739 and NM_014139, respectively.

Where promoters or promoter sequences are not previously known, they can be obtained or determined using standard molecular biology techniques, beginning with knowledge of a complete or partial cDNA sequence of a nociceptive receptor or ion channel. It is noted in this regard that essentially complete genomic sequences are already available for a number of mammalian species, including humans and mice.

As used herein the term "test cell that expresses Runx1" refers to any cell that expresses a Runx1 protein. In a preferred embodiment the Runx1 protein includes a Runt domain that is capable of binding to DNA. In one embodiment the test cell that expresses Runx1 is a neuronal cell, i.e., a neuron, that naturally expresses Runx1. In one embodiment the test cell is a neuron in or derived from a dorsal root ganglion or trigeminal ganglion. The test cell can be isolated, i.e., removed from its usual environment as it is found in nature. In one embodiment the test cell is an immortalized cell, e.g., a cell from a cell line. In one embodiment the test cell that expresses Runx1 is a cell that has been altered to overexpress Runx1; such a cell can be a neuron or it can be a cell other than a neuron. A cell can be altered to overexpress Runx1 by introduction into the cell of a nucleic acid that includes a coding sequence for Runx1, e.g., a Runx1 expression vector. The nucleic acid that includes a coding sequence for Runx1 can be incorporated into the genome of the cell or it can be present in the cell as a plasmid or other form of nucleic acid that is separate from the genomic DNA of the cell. In one embodiment the test cell that has been altered to overexpress Runx1 is a cell that is transiently transfected with a nucleic acid that includes a coding sequence for Runx1. In one embodiment the test cell that has been altered to overexpress Runx1 is a cell that is stably transfected with a nucleic acid that includes a coding sequence for Runx1. In one embodiment the test cell that has been altered to overexpress Runx1 is a cell that normally does not express Runx1. The overexpression of Runx1 can be constitutive or it can be conditional, e.g., dependent on the presence or absence of an agent that regulates its expression by interaction with a control element associated with the nucleic acid coding for Runx1.

As used herein, the term "Runx1 expression vector" refers to any nucleic acid construct that includes a nucleic acid that includes a coding sequence for Runx1, operatively linked to a gene expression sequence which is capable of directing the expression of the Runx1 nucleic acid within a eukaryotic cell. The gene expression sequence is any regulatory nucleotide sequence, such as a promoter sequence or promoter-enhancer combination, which facilitates the efficient transcription and translation of the Runx1 nucleic acid to which it is operatively linked. The gene expression sequence may be, for example, a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, β-actin, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined Runx1 nucleic acid. The gene expression sequences optionally include enhancer sequences or upstream activator sequences as desired.

The Runx1 nucleic acid is operatively linked to the gene expression sequence. As used herein, a nucleic acid coding sequence and a gene expression sequence are said to be operatively linked when they are covalently linked in such a way as to place the expression or transcription and/or translation of the coding sequence under the influence or control of the gene expression sequence. As used herein, the Runx1 nucleic acid sequence and the gene expression sequence are said to be operatively linked when they are covalently linked in such a way as to place the expression or transcription and/or translation of the Runx1 coding sequence under the influence or control of the gene expression sequence. Two DNA sequences are said to be operatively linked if induction of a promoter in the 5' gene expression sequence results in the transcription of the Runx1 sequence and if the nature of the linkage between the two DNA sequences does not (1) result in the introduction of a frame-shift mutation, (2) interfere with the ability of the promoter region to direct the transcription of the Runx1 sequence, or (3) interfere with the ability of the corresponding RNA transcript to be translated into a protein. Thus, a gene expression sequence would be operatively linked to a Runx1 nucleic acid sequence if the gene expression sequence were capable of effecting transcription of that Runx1 nucleic acid sequence such that the resulting transcript is translated into the desired protein or polypeptide.

The Runx1 nucleic acid of the invention may be delivered to the cell alone or in association with a vector. In its broadest sense, a vector is any vehicle capable of facilitating the transfer of the Runx1 nucleic acid to a cell so that Runx1 can be expressed by the cell. The vector generally transports the nucleic acid to the cell with reduced degradation relative to the extent of degradation that would result in the absence of the vector. The vector optionally includes the above-described gene expression sequence to enhance expression of the Runx1 nucleic acid in cells. In general, the vectors useful in the invention include, but are not limited to, plasmids, phagermids, viruses, and other vehicles derived from viral or bacterial sources that have been manipulated by the insertion or incorporation of the Runx1 nucleic acid sequences. Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Krieger, M., Gene Transfer and Expression: A Laboratory Manual, W.H. Freeman and Co., New York (1991) and Murray, E. J., Methods in Molecular Biology, vol. 7, Humana Press, Inc., Clifton, N.J. (1991).

A preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages, including hematopoietic cells; and lack of super infection inhibition, thus allowing multiple series of transductions. Reportedly, the adeno-associated virus can integrate into human cellular DNA in a site-specific manner, thereby minimizing the possibility of insert ional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extra chromosomal fashion.

Other vectors include plasmid vectors. Plasmid vectors have been extensively described in the art and are well-known to those of skill in the art. See, e.g., Sam brook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRc/CMV, SV40, and pBlueScript. Other plasmids are well-known to those of ordinary skill in the art. Additionally, plasmids may be custom designed using restriction enzymes and ligation reactions to remove and add specific fragments of DNA.

As used herein, the term "test agent" refers to any suitable chemical compound or mixture of chemical compounds selected for assessment in a screening method of the invention. Test agents specifically include but are not limited to small molecules, nucleic acids, polysaccharides, peptides, polypeptides, proteins, lipids, and conjugates of any combination thereof.

In one embodiment a test agents is a small molecule, i.e., a natural, synthetic, or semi-synthetic organic molecule with molecular weight less than 1.5 kDa. Many drugs are small molecules, and the test agent in one embodiment is a drug.

In one embodiment the test agent is nucleic acid. The nucleic acid can be DNA, RNA, or a synthetic homolog thereof, e.g., a peptide nucleic acid or a phosphorothioate nucleic acid. The nucleic acid in one embodiment can be a competitor for a nucleic acid that is bound by the Runt domain of Runx1, e.g., a nucleic acid having a sequence 5'-YGYGGT-3' or 5'-PYGPYGGT-3'. In various specific embodiments 5'-YGYGGT-3' can be 5'-CGCGGT-3', 5'-CGTGGT-3', 5'-TGCGGT-3', or 5'-TGTGGT-3'. In various specific embodiments 5'-PYGPYGGT-3' can be 5'-GTGGTGGT-3', 5'-GCGGTGGT-3', 5'-ATGGTGGT-3', 5'-ACGGTGGT-3', 5'-GTGGCGGT-3', 5'-GCGGCGGT-3', 5'-ATGGCGGT-3', 5'-ACGGCGGT-3', 5'-GTGATGGT-3', 5'-GCGATGGT-3', 5'-ATGATGGT-3', 5'-ACGATGGT-3', 5'-GTGACGGT-3', 5'-GCGACGGT-3', 5'-ATGACGGT-3', or 5'-ACGACGGT-3'.

In one embodiment the test agent nucleic acid can be an antisense nucleic acid targeted to a DNA or RNA sequence encoding or regulating the expression of: Runx1; a Runx1 cofactor (e.g., CBFβ); or a Runx1-dependent nociceptive receptor or ion channel. In one embodiment the test agent nucleic acid can be a short interfering RNA (siRNA) targeted to a DNA or RNA sequence encoding Runx1, a Runx1 cofactor (e.g., CBFβ), or a nociceptive receptor or ion channel.

In one embodiment the test agent nucleic acid encodes a protein for expression within a cell upon its introduction into the cell. The protein encoded by such a nucleic acid in one embodiment can be a protein that modulates the interaction between Runx1 and a Runx1 cofactor or other protein (such as CBFβ) that interacts with Runx1. In one embodiment the protein encoded by such a nucleic acid is a dominant negative CBFβ.

A test agent can belong to a library of small molecules or a library of test agents, where the library may include tens, hundreds, thousands, tens of thousands, or even hundreds of thousands of compounds. In one embodiment the library is or includes a number of compounds generated through combinatorial chemistry techniques. A library can be presented in the form of a physical array and may in one embodiment be accessed or otherwise manipulated using a robotic device, particularly for high throughput screening.

Certain methods according to the invention involve comparison between a test cell and a control cell. As used herein, the term "control cell" refers to any cell suitable for use in the methods of the invention for comparison with a test cell. In preferred embodiments the test cell and the control cell are derived from the same or homologous source of cells. For example, in one embodiment a test cell that expresses Runx1 is compared to a control cell that does not express Runx1, where the test cell and the control cell differ insofar as the test cell includes a Runx1 expression vector but the control does not include the Runx1 expression vector. As a further example, in one embodiment a test cell that is contacted with a test agent is compared to a control cell that is not contacted with the test agent.

In certain embodiments measurements comparing the test cell to the control cell are performed under conditions (e.g., test conditions) that are identical. The test conditions can include such parameters as temperature, culture medium, concentration of test agent, cell density, duration, and the like. Those skilled in the art will recognize how to design and perform properly controlled comparisons.

In one embodiment a candidate inhibitor of Runx1-mediated expression of a nociceptive receptor or ion channel identified according to a method of the invention is tested in a further assay designed to establish whether the inhibitory effect of the candidate agent is specifically attributable to inhibition of Runx1 expression or function. Such an assay can compare, for example, the expression of the nociceptive receptor or ion channel in a cell that expresses Runx1 versus the expression of the nociceptive receptor or ion channel in a cell that does not expresses Runx1.

Similarly, in one embodiment a candidate agent for use in inhibiting neuropathic pain identified according to a method of the invention is tested in a further assay designed to establish whether the inhibitory effect of the candidate agent is specifically attributable to inhibition of Runx1 expression or function. Such an assay can compare, for example, the expression of the nociceptive receptor or ion channel in a cell that expresses Runx1 versus the expression of the nociceptive receptor or ion channel in a cell that does not expresses Runx1.

Certain methods according to the invention involve the use of a reporter. As used herein, the term "reporter" refers to any nucleic acid or proteinaceous molecule, including a protein, that is produced in or by a cell and that can be measured, preferably by objective, quantitative measurement. In one embodiment the reporter is a protein that is normally not expressed by the cell. The reporter can be encoded by a nucleic acid sequence the expression of which is placed under the control of a promoter that is sensitive to a selected condition or compound, e.g., Runx1. Examples of such reporters are well known in the art. In one embodiment the reporter is a protein, such as green fluorescent protein, that emits light. The emitted light can be measured in a quantitative manner using a luminometer or other suitable device. The intensity of emitted light will be directly proportional to the amount of reporter protein that is expressed. In one embodiment the reporter is an enzyme that is capable of converting a suitable enzyme substrate into a product. The product can be measured using any suitable quantitative method, examples of which are well known in the art. The amount of product in the presence of nonlimiting substrate will be directly proportional to the amount of reporter enzyme that is expressed.

Certain methods of the invention in some embodiments involve measuring expression of a particular protein or transcript. General methods and techniques for making such measurements are well known in the art and can include, without limitation, immunostaining, in situ hybridization, fluorescence microscopy, enzyme-linked immunosorbent assay (ELISA), immunoblotting (e.g., Western or dot blotting), Northern blotting, reverse transcriptase/polymerase chain reaction (RT/PCR), etc. Those skilled in the art will recognize that suitable target-specific binding agents and probes can be obtained commercially or prepared using standard techniques. For example, nucleic acid probes can be prepared using publicly available sequences of target sequences and a suitable tagging agent. Antigen-specific polyclonal and monoclonal antibodies can be prepared and, optionally, labeled using suitable sources of antigen and standard techniques in molecular biology.

The invention in certain aspects provides a method for identifying a candidate agent for use in inhibiting neuropathic pain and/or cancer pain. As used herein, the term "neuropathic pain" refers to heightened pain sensitivity associated with peripheral nerve injury. The nerve injury may arise as a result of mechanical injury or disease affecting the nerve. In an important clinical setting, neuropathic pain is associated with cancer. Neuropathic pain can be associated with mechanical allodynia, i.e., pain stimulated by a normally innocuous tactile stimulus. Neuropathic pain typically has an unusual burning, tingling, or electric shock-like quality and can be triggered by very light touch. Damaged primary afferents, including nociceptors, become highly sensitive to mechanical stimulation and generate impulses even in the absence of stimulation.

The invention in one aspect involves measuring an amount of binding between Runx1 and a Runx1-sensitive promoter. The measuring can be performed using any suitable method, including but not limited to chromatin immunoprecipitation (ChIP) and surface plasmon resonance (SPR). In ChIP samples containing Runx1 promoter protein and putative promoter-containing DNA are chemically fixed using paraformaldehyde or other suitable agent, thereby crosslinking promoter to DNA. Following crosslinking, samples are sonicated to produce DNA fragments on the order of 1 kb long, some of which will be crosslinked to promoter. Upon addition of anti-Runx1 antibody, Runx1 and associated DNA can be precipitated or otherwise isolated from material not containing Runx1, and then bound DNA can be extracted from the Runx1, for example by heating. Quantitative PCR performed using extracted DNA as template and primers selected for specific nociceptive receptors and ion channels can then be performed to assess the amount of binding between Runx1 and a Runx1-sensitive promoter.

Based on discoveries underlying the invention, it is now appreciated that Runx1 coordinately controls expression of a number of nociceptive receptors and ion channels. The methods of the invention can be used to assess the effect of a test agent on a number of nociceptive receptors and ion channels in parallel, thereby powerfully facilitating methods for discovery of candidate agents for use in inhibiting Runx1-mediated expression of nociceptive receptors and ion channels, as well as neuropathic pain.

The present invention is further illustrated by the following Examples, which in no way should be construed as further limiting.

EXAMPLES

Example 1

Generation and Characterization of Runx1$^{-/-}$ Mice

Two Runt class transcription factors, Runx1/PEBP2αB/AML1 (Runx1) and Runx3/PEBP2βC/AML2 (Runx3; de Bruijn M F et al. (2004) *Oncogene* 23:4238-8), are expressed by cutaneous and proprioceptive sensory neurons, respectively, in the dorsal root ganglia (DRG), and Runx3 is implicated in the differentiation of proprioceptive sensory neurons. Inoue K et al. (2002) *Nat Neurosci* 5:946-54; Levanon D et al. (2002) *EMBO J* 21:3454-63; Theriault F M et al. (2004) *Proc Natl Acad Sci USA* 101:10343-8. To examine the influence of Runx1 on the differentiation of nociceptive sensory neurons, the phenotype of Runx1-deficient mice were analyzed. Mice carrying a loxP-based conditional Runx1 allele (referred here to as Runx1$^{F}$) were crossed with a Wnt1-Cre mouse strain that directs Cre expression in neural crest progenitors of DRG neurons.

Wnt1-Cre transgenic mice have been described previously. Jiang X et al. (2000) *Development* 127:1607-16. The morning that vaginal plugs were observed was considered as E0.5. PCR-based genotyping was performed with the following primers: for Wnt1-Cre allele, 5' TATCTCACGTACTGACG-GTG 3' (SEQ ID NO:1) and 5' CTAGTCTAGACTAATCGC-CATCTTCCAGC 3' (SEQ ID NO:2); for Runx1 wild-type and floxed alleles, 5' GAGTCCCAGCTGTCAATTCC 3' (SEQ ID NO:3) and 5' GGTGATGGTCAGAGTGAAGC 3' (SEQ ID NO:4), with floxed allele showing a larger size of DNA band after gel electrophoresis.

In Situ Hybridization and Immunostaining. Mouse in situ probes for TRPA1 (0.9 kb), TRPM8 (0.71 kb), TRPV1 (0.72 kb), TrkA (0.7 kb), TRPV2 (0.8 kb), DRASIC (1.0 kb), P2X3 (1.1 kb), TRPC3 (0.8 kb), and Nav1.9 were amplified with gene-specific sets of PCR primers and cDNA templates prepared from P0 mouse DRG. The probes of Mrgpra1-8, Mrgprd, Mrgprc, Mrgprb4-5 were gifts from X. Zhong and D. J. Anderson. The in situ signals were photographed under transluminescent light and converted into pseudo red fluorescent color.

For immunostaining on frozen sections, embryos were collected in ice-cold PBS, fixed in 4% paraformaldehyde in PBS, and saturated with 20% sucrose in PBS overnight at 4° C. For adult mice, after they were perfused with 4% paraformaldehyde in PBS, dorsal root ganglia were dissected and collected in 4% paraformaldehyde for 1 hour, and saturated with 20% sucrose in PBS overnight at 4° C. Adjacent sections of 14 μm thickness were blocked with 1% BSA plus 0.1% Triton in PBS for 1 hour, and incubated at 4° C. overnight with rabbit or guinea pig anti-Runx1 (T. Jessell, Columbia University). The primary antibodies were detected using species-specific fluorescence-conjugated secondary antibodies.

Cell Counting. To count total DRG neurons, fifth lumbar (L5) DRG were dissected from three pairs of Runx1$^{-/-}$ and control Runx1$^{F/F}$ mice, fixed, and embedded, sectioned with 10 μm thickness, hybridized with a digoxigenin-labeled non-radioactive RNA probe of SCG10, which is a pan-neural marker. The in situ hybridization signal was detected by anti-digoxigenin antibody conjugated with alkaline phosphatase that can produce a purple color enzymatic reaction product. Numbers of SCG10$^{+}$ neurons were counted. Only cells containing nuclei were counted. To determine the percentages of neurons expressing molecular markers, four adjacent sets of sections were prepared from lumbar DRG and probed separately with four different probes, one of which was the pan-neural marker SCG10 to determine the total number of neurons so that percentages can be calculated. Three independent lumbar DRG were used for each counting. Instead of relying on morphology to identify neurons, the total neuron number was determined by counting cells expressing SCG10. This method made it possible to identify some very small sensory neurons. The in situ hybridization methods also made it possible to identify Ret$^{+}$ neurons that expressed at medium/low levels.

Results are shown in FIG. 2, which illustrates conditional knockout of Runx1 in the DRG and comparison of neurogenesis between wild-type and Runx1-deficient mice. FIG. 2A presents schematics of the conditional allele. Numbered vertical bars represent exons. Exon 4, encoding part of the DNA-binding Runt domain, is flanked with two loxP sequences (white triangles). Deletion of this exon is known to generate a null allele. de Bruijn M F et al. (2004) *Oncogene* 23:4238-8. The neo cassette in the intron region was also flanked with loxP sequences. FIG. 2A illustrates how, after crossing with Wnt1-Cre nice, the neo cassette and exon 4 were removed by Cre-mediated DNA recombination, thereby yielding Runx1$^{-/-}$ mice. FIG. 2B illustrates immunostaining of Runx1 on sections through wild-type Runx1$^{F/F}$ (left) and Runx1$^{-/-}$ (right) adult DRG. A complete loss of Runx1 protein was noted in mutants. FIG. 2C illustrates that expression of the pan-neuronal marker SCG10, detected by in situ hybridization, was comparable in wild-type Runx1$^{F/F}$ (left) and Runx1$^{-/-}$ (right) adult DRG. FIG. 2D illustrates that no difference was detected in numbers of SCG10$^{+}$ neurons in the fifth lumbar (L5) DRG between wild-type Runx1$^{F/F}$ and Runx1$^{-/-}$ mice.

In Runx1$^{-/-}$ mice there was no detectable expression of Runx1 in DRG neurons, suggesting complete penetrance of Cre-mediated recombination. Runx1$^{-/-}$ mice were viable and fertile with no overt abnormalities. Moreover, DRG neuronal numbers were similar in Runx1$^{-/-}$ and control Runx1$^{F/F}$ mice, indicating that Runx1 is not required for the genesis or survival of DRG neurons.

Example 2

Runx1 Promotes Transition from TrkA$^{+}$ to Ret$^{+}$ Phenotype

In Runx1$^{-/-}$ mice, the transition from TrkA to Ret expression is markedly impaired, resulting in a dramatic change in the proportional representation of TrkA$^{+}$ and Ret$^{+}$ neurons (FIG. 3). Experiments in this example examined the role of Runx1 in the transition of neurons from a TrkA$^{+}$ phenotype to a Ret$^{+}$ phenotype.

For in situ hybridization and immunostaining on frozen sections, transverse sections through DRGs or the dorsal horn of the spinal cords of adult mice were collected and prepared for in situ hybridization with digoxigenin-labeled TrkA and Ret riboprobes. The in situ hybridization signal was detected by anti-digoxigenin antibody conjugated with alkaline phosphatase that can produce a purple color enzymatic reaction product (which was converted into pseudo red fluorescent color using Photoshop®). After detection of in situ hybridization signals, the tissue sections were incubated with fluorescein-conjugated IB4 lectin. Representative results are shown in FIG. 3.

As shown in FIG. 3, Runx1 regulates neurotrophin receptor expression. FIG. 3A-D show results of in situ hybridization with TrkA (FIG. 3A and FIG. 3B) or Ret (FIG. 3C and FIG. 3D) probes of adult DRGs in wild-type (FIG. 3A and FIG. 3C) and Runx1$^{-/-}$ (FIG. 3B and FIG. 3D) mice. FIG. 3E-H show results from double labeling for TrkA or Ret and IB4 binding in adult DRG in wild-type (FIG. 3E and FIG. 3G) and Runx1$^{-/-}$ (FIG. 3F and FIG. 3H) mice. In wild-type DRG, IB4$^+$ cells coexpress Ret (FIG. 3E, arrow), but do not coexpress TrkA (FIG. 3G, arrow). In contrast, in adult Runx1$^{-/-}$ DRG, IB4$^+$ neurons lose Ret expression (FIG. 3F, arrow), and many of them express TrkA instead (FIG. 3H, arrow). FIG. 3I shows percentages of DRG neurons expressing the molecular markers in wild-type and Runx1$^{-/-}$ mice. FIG. 3J shows a schematic of the transformation of prospective Ret$^+$ into TrkA$^+$ nociceptors in mutants (in comparison with the situation occurring in wild-type DRG, FIG. 1G). In Runx1$^{-/-}$ mice all nociceptors retain TrkA expression, although the "transformed" cells retain IB4 staining.

In P60 DRG, the proportion of Ret$^+$ neurons decreased from 69% in control (Runx1$^{F/F}$) mice to 30% in Runx1$^{-/-}$ mice (FIG. 3C, FIG. 3D and FIG. 3I; Table 1). Conversely, the proportion of TrkA$^+$ neurons increased from 28% in control mice to 69% in Runx1$^{-/-}$ mice (FIG. 3A, FIG. 3B, and FIG. 3I; Table 1). The degree of loss of Ret$^+$ and gain in TrkA$^+$ neurons in Runx1$^{-/-}$ mice agreed well with the proportion of adult DRG neurons that express Runx1 in wild-type mice (~40%, Table 1). In wild-type DRG, carbohydrate epitopes recognized by the lectin IB4 labeled ~70% of mature Runx1$^+$ neurons, while IB4 label was not detected in TrkA$^+$ nociceptors (FIG. 3G). IB4 labeling persisted in Runx1$^{-/-}$ mice (FIG. 3F, 3H), but most labeled neurons no longer expressed Ret and many now expressed TrkA instead (FIG. 3H). Together, these findings provide evidence that Runx1 activity is normally involved in promoting the transition from a TrkA$^+$ to a Ret$^+$ phenotype, by suppressing TrkA and activating or maintaining Ret expression (FIG. 3J).

prb4, Mrgprb5, Mrgprd, Mrgpra1-8, Mrgprc, Nav1.9, and DRASIC (1.0 kb). Mouse in situ probes for TRPA1, TRPM8, TRPC3, TRPV1, TRPV2, P2X3, Nav1.9, and DRASIC were amplified with gene-specific sets of PCR primers and cDNA templates prepared from P0 mouse DRG. The probes of Mrgpra1-8, Mrgprd, Mrgprc, Mrgprb4-5, which contain the coding region, were gifts from X. Zhong and D. J. Anderson at California Institute of Technology. In one set of experiments sections were double labeled using anti-Runx1 antibody and a probe for TRPM8, Mrgprd, P2X3, Nav1.9, TRPC3, or DRASIC, essentially as described in Example 1.

For in situ hybridization combined with fluorescent immunostaining for Runx1, in situ hybridization was performed without proteinase K treatment, followed by immunostaining with Runx1 antibody (gift from T. Jessell, Columbia University, New York; 1:4000 in blocking solution) that was against the peptide sequence GRASGMTSLSAELSSRL (SEQ ID NO:5). The specificity of Runx1 antibody was confirmed by the matching of its expression in wild-type DRG and the elimination of its staining in Runx1$^{-/-}$ DRG. The in situ signals were photographed under trans-luminescent light and converted into pseudo red fluorescent color, while Runx1 protein was detected with Alexa 488-conjugated secondary antibodies (Jackson Laboratories). Representative results are shown in FIG. 4.

As shown in FIG. 4A-D, there was marked reduction of diverse ion channels and receptors in DRG of Runx1$^{-/-}$ mice as compared to wild-type (Runx1$^{F/F}$) mice. In particular there was a selective reduction of high-level expression (arrows), but not of intermediate level expression (arrowheads), of TRPV1, TRPV2, and Nav1.9 in Runx1$^{-/-}$ mice. Only very few Runx1$^{-/-}$ cells still exhibited high-level expression of TRPV2 or Nav1.9.

Figure 4A:
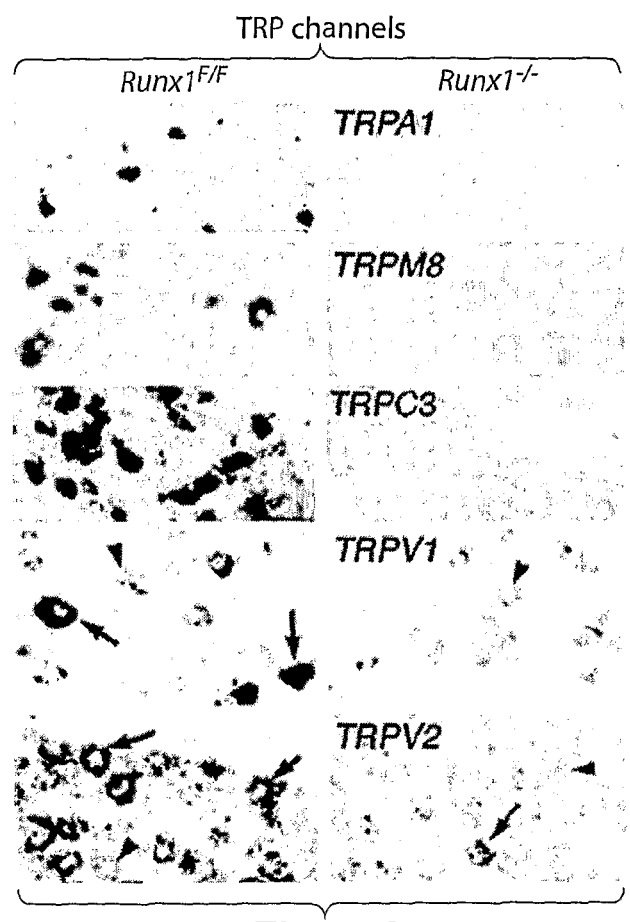
Figure 4B:
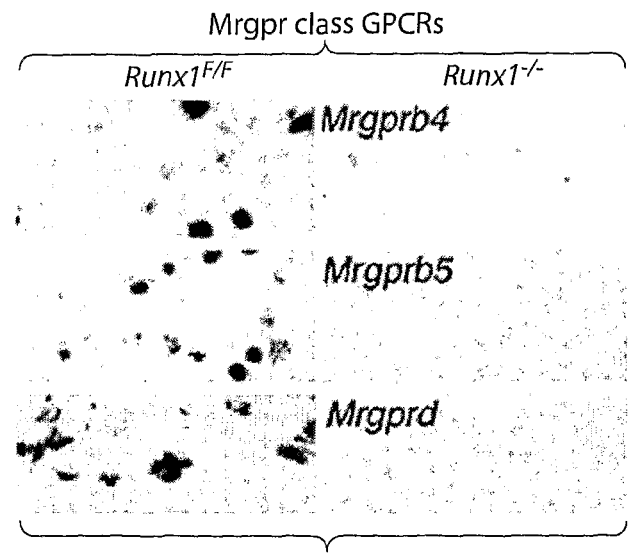
Figure 4C:
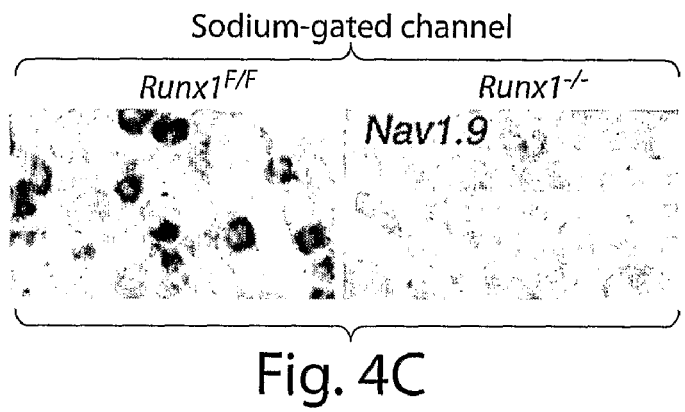
Figure 4D:
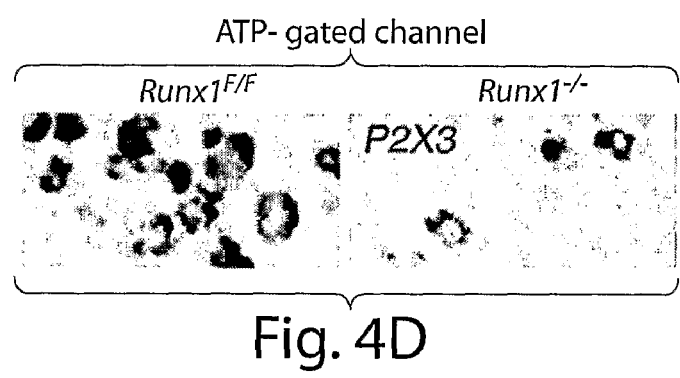
Figure 4E:
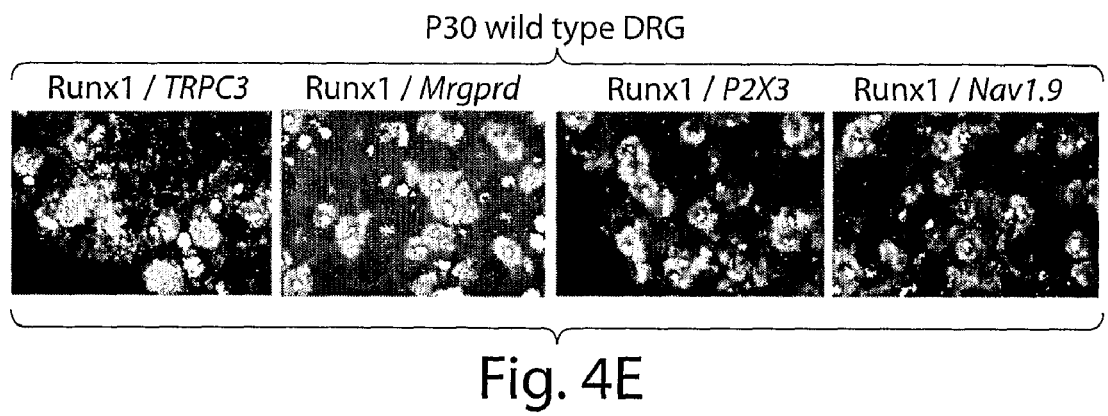

As shown in FIG. 4E, double labeling of Runx1 protein (bright, originally green) and indicated probes (less bright, originally red) for TRPC3, Mrgprd, P2X3, or Nav1.9/SNS on adult P30 wild-type DRG sections demonstrated that Runx1 was expressed in the majority of neurons expressing TRPC3, Mrgprd, P2X3, or Nav1.9/SNS. Runx1 was also expressed in the majority of neurons expressing TRPM8.

TRP class ion channels transduce a wide range of thermal stimuli, including noxious cold or heat. Jordt S E et al. (2003)

TABLE 1

Percentages of Neurons Expressing Molecular Markers in Runx1$^{F/F}$ and Runx1$^{-/-}$ DRG

|  | SCG10 | Runx1 | TrkA | Ret | IB4 | TrkC | Mrgpra1 | Mrgpra2 | Mrgpra3 | Mrgpra6 |
|---|---|---|---|---|---|---|---|---|---|---|
| Runx1$^{F/F}$ | 100 | 40 ± 2 | 28 ± 3 | 69 ± 6 | 30 ± 4 | 12 ± 1 | 37 ± 7 | 52 ± 6 | 6 ± 2 | 43 ± 6 |
| Runx1$^{-/-}$ | 101 ± 5 | 0 ± 0* | 69 ± 6* | 30 ± 2* | 31 ± 5 | 12 ± 1 | 4 ± 2* | 20 ± 4* | 1 ± 0.2* | 4 ± 2* |

Values presented as mean ± s.d.
*P < 0.001 (by Student's test)

Example 3

Runx1 is Involved in Coordinate Expression of Multiple Nociceptors

Experiments in this example were performed to compare expression of multiple, diverse nociceptive sensory channels and receptors in DRG taken from adult wild-type and Runx1$^{-/-}$ mice.

For in situ hybridization and immunostaining on frozen sections, transverse sections through DRGs of adult mice were collected and prepared for in situ hybridization with probes for TRPA1 (0.9 kb), TRPM8 (0.71 kb), TRPC3 (0.8 kb), TRPV1 (0.72 kb), TRPV2 (0.8 kb), P2X3 (1.1 kb), Mrg- Curr Opin Neurobiol 13:487-92; Bandell M et al. (2004) Neuron 41:849-57. In Runx1$^{-/-}$ mice, there was a virtually complete elimination of two putative cold receptors TRPA1 and TRPM8 (Jordt S E et al. (2003) Curr Opin Neurobiol 13:487-92; Bandell M et al. (2004) Neuron 41:849-57) as well as of TRPC3 (FIG. 4A). High level expression of two heat receptors TRPV1 and TRPV2 (Jordt S E et al. (2003) Curr Opin Neurobiol 13:487-92) was also largely eliminated (FIG. 4A).

The Mrgpr genes (Mrgpr/SNSR) encode a large family of G-protein coupled receptors (GPCRs) expressed preferentially in Ret$^+$ nociceptors (Dong X et al. (2001) Cell 106:619-32; Lembo P M et al. (2002) Nat Neurosci 5:201-9), and activation of Mrgprc in rats causes hypersensitivity to heat and mechanical stimuli (Grazzini E et al. (2004) *Proc Natl Acad Sci USA* 101:7175-80). In Runx1$^{-/-}$ mice, expression of all twelve Mrgpr genes was either markedly reduced or absent (FIG. 4B, Table 1).

ATP, released from damaged tissue, evokes painful response by activating ATP-gated channels (P2Xs). Wood J N (2004) *Gut* 53 Suppl 2, ii9-12. Expression of nociceptor-specific P2X3 (Chen C C et al. (1995) *Nature* 377:428-31) was markedly reduced in Runx1$^{-/-}$ mutants (FIG. 4C).

The tetrodotoxin-resistant Na$^+$ channel gene Nav1.9/SNS2 determines nociceptor membrane excitability (Dib-Hajj S D et al. (1998) *Proc Natl Acad Sci USA* 95:8963-8), and again in Runx1$^{-/-}$ mice, Nav1.9/SNS2 expression was markedly reduced (FIG. 4D, Table 1).

Double labeling showed that Runx1 is detected in a majority of neurons expressing TRPM8, TRPC3, Mrgprd, Nav1.9 or P2X3 (FIG. 4E). These findings suggest that Runx1 is involved in the expression of a large cohort of nociceptive ion channels and receptors.

Example 4

Runx1 Suppresses Expression of Certain Neuropeptides and Ion Channels

FIG. 5 illustrates that Runx1 is able to suppress the expression of markers normally expressed in TrkA+ nociceptors. Most adult TrkA$^+$ neurons are peptidergic and express the genes encoding the precursors for the neuropeptides Substance P (SP) and Calcitonin Gene Related Peptide (CGRP). Snider W D et al. (1998) *Neuron* 20:629-32. From E16.5 to P30 in wild-type DRG, CGRP$^+$ neurons either do not express, or express only a low level of, Runx1 (FIG. 5A). In Runx1$^{-/-}$ adult mice, however, there is a marked increase in the percentages of DRG neurons expressing CGRP, from 32±2% to 64±2% (P<0.001) (FIG. 5C, E). SP$^+$ neurons also showed a significant, albeit more modest, increase in the percentages of DRG neurons expressing CGRP, from 32±4% to 43±2% (P<0.0001) (FIG. 5C, E). The expansion of CGRP in Runx1$^{-/-}$ nice was also apparent by the detection of CGRP expression in IB4$^+$ neurons (FIG. 5C), which is only very rarely observed in wild-type DRG (FIG. 5C). Together, these findings suggest that in absence of Runx1, prospective non-peptidergic nociceptors develop into CGRP$^+$ peptidergic neurons.

The DRG acid-sensing channel DRASIC and the mu-class opioid receptor (MOR) are associated preferentially in peptidergic neurons. Consistently, in adult wild-type DRG Runx1$^+$ neurons do not express DRASIC (FIG. 5A). In Runx1$^{-/-}$ adult mice, however, there was a marked increase in the percentages of DRG neurons expressing MOR (from 33±2% to 63±3%; P<0.001) or DRASIC (from 22±2% to 71±5%; P<0.001) (FIG. 5D, E). Thus, within presumptive Ret$^+$ neurons, Runx1 is required to suppress the expression of a subset of receptors and ion channels normally associated with a TrkA identity (summarized in FIG. 5F).

Example 5

Expression of Certain Nociceptor Receptors or Channels is Independent of Runx1

FIGS. 5D and 5E (Example 4) also show that not all nociceptor receptors or channels are affected in Runx1$^{-/-}$ mice. There was no increase or reduction in expression of the acid-sensing channel ASIC in Runx1$^{-/-}$ mice as compared to wild-type mice. The expression of ion channel Nav1.8/SNS was also unaffected in Runx1$^{-/-}$ mice as compared to wild-type mice. Thus, Runx1 deficiency results in a selective loss in expression of a subset of nociceptor transduction proteins.

Example 6

Runx1 Initiates Expression of some Ion Channels and Receptors Independent of TrkA and Ret Analysis of Runx1 phenotypes at prenatal stages further suggested that Runx1 initiates expression of some ion channels/receptors before it suppresses TrkA and maintains Ret expression postnatally (FIG. 6). These findings suggested that the loss of at least some ion channels/receptors in Runx1$^{-/-}$ mice is independent of the loss of Ret or the gain of TrkA.

In situ hybridization showed that expression of TRPM8 and Mrgprd is first detected at E16.5 in wild-type DRG (FIG. 6A, C), and this expression is eliminated in Runx1$^{-/-}$ DRG at E16.5 (FIG. 6, D). However, at every embryonic or neonatal stage examined (E14.5, E17, and P0) nearly all Runx1$^+$ neurons in wild-type DRG expressed TrkA (FIG. 6E). This suggests that Runx1 is required to activate channel/receptor expression at prenatal/neonatal stages before it acts to switch off TrkA expression at postnatal stages. By E17, Ret expression becomes apparent in a subpopulation of Runx1$^+$ neurons (FIG. 6F). At this stage, however, TRPM8$^+$ neurons do not co-express Ret (FIG. 6G-I), suggesting that initiation of TRPM8 expression is independent of Ret-mediated signaling. Thus, the loss of many nociceptive ion channels in Runx1$^{-/-}$ DRG neurons is unlikely be explained solely by the loss of Ret or the gain of TrkA expression, which in turn implies a more direct function for Runx1 in controlling the expression of these channels and receptors.

Example 7

Runx1 Controls Central Targeting of Nociceptive Afferents

The precision in processing sensory information demands coordination between the specification of sensory modality and afferent central target selection. FIG. 7 shows that Runx1 coordinates these two developmental processes. In wild-type mice, IB4$^+$ (Ret$^+$) afferents project predominantly to inner lamina II (IIi) (FIG. 7A (arrow) and FIG. 7K), whereas CGRP$^+$ and SP$^+$ peptidergic afferents (TrkA$^+$) project predominantly to lamina I and outer layer II (IIo) (FIG. 7C, arrowhead), and to a lesser extent to lamina IIi (FIG. 7C, arrow). Snider W D et al. (1998) *Neuron* 20:629-32. In Runx1$^{-/-}$ mice, IB4$^+$, CGRP$^+$, and SP$^+$ afferents all reach the dorsal horn (FIG. 7B, D, H), suggesting that initial axon pathfinding from the DRG to the spinal cord is independent of Runx1. However, double labeling of IB4 and CGRP or SP clearly showed a shift in IB4$^+$ afferent innervation from the more ventral lamina to the most dorsal lamina of the dorsal horn, whereas CGRP$^+$ afferents (FIG. 7D versus 7C) and SP$^+$ afferents (FIG. 7H versus 7G) still project predominantly to the most superficial lamina. The dorsal shift in IB4$^+$ afferent innervation is also supported by the double labeling of IB4 and PKC-gamma (FIG. 7I). In wild-type mice, IB4$^+$ afferents terminate in the lamina exactly abutting the territory enriched with PKC-gamma-positive neuronal cell bodies and processes (FIG. 7I), but in Runx1$^{-/-}$ mice the density of IB4$^+$ afferents in this area is greatly reduced (FIG. 7J versus FIG. 7I, arrows).

In the dorsal horn of Runx1$^{-/-}$ mice, a subset of IB4$^+$ afferents co-stained with CGRP and to a lesser extent with SP, something rarely seen in wild-type mice. This difference in co-labeling with CGRP and SP is consistent with their dramatic (CGRP) and modest (SP) derepression in Runx1$^{-/-}$/IB4$^+$ neurons (FIG. 5). However, within the superficial dorsal lamina of Runx1-deficient mice, some afferents express only CGRP or SP and do not label with IB4. This suggests that endogenous peptidergic afferents project normally in Runx1$^{-/-}$ mice. Thus a loss of Runx1 appears to specifically perturb the laminar target selection of IB4$^+$ afferents (summarized in FIG. 7K, L).

Example 8

Runx1-Deficient Mice Exhibit Markedly Diminished Response to Noxious Thermal Stimuli To examine if the molecular and anatomical defects in Runx1$^{-/-}$ mice are accompanied by alterations in behavioral responses to noxious stimuli, acute responses to noxious thermal and mechanical stimuli were assayed.

All animals were acclimatized to the behavioral testing apparatus on at least three 'habituation' sessions. Following habituation, at least two baseline measures were obtained for each of the behavioral tests on two separate occasions the week before experimental measurements. The tester was blinded to the genotype of each animal.

To measure cold pain, animals were placed on an elevated wire grid. A drop of acetone was applied to the plantar hindpaw using a feeding tube attached to a syringe. The duration of time that the animal elevated or licked the paw over a 90 s period immediately following application of the acetone drop was measured.

To measure heat pain, mice were placed on a hot plate (Ugo Basile, Italy) and the latency to hindpaw flicking, licking, or jumping measured. The hot plate was set to three different temperatures, 50, 52, and 55° C., and all animals were tested sequentially at each temperature with at least 5 min between tests. A cutoff time of 60 s was used for testing at 50° C.

To measure mechanical pain, animals were placed on an elevated wire grid and the lateral plantar surface of the hindpaw stimulated using von Frey monofilaments (0.0174-4.57 g) or pin prick. The withdrawal threshold for the von Frey assay was determined as the filament at which the animal withdrew its paw at least twice in 10 applications. The pin prick was measured as duration of time that the animal elevated or licked the paw over a 20 s period immediately following the pin prick.

Statistical analyses of pain behaviors. Baseline data (and all non-procedural testing data) was taken as the mean of two tests performed. Except as noted otherwise, behavioral data were analyzed by Student's T-test when comparing two groups (Graphpad Prism, Graphpad, San Diego, Calif.) and 2-way repeated measures ANOVA followed by Bonferroni's post-test for time courses of two or more groups (R, v. 1.7.0, R Development Core Team, Vienna, Austria). Log data was used for statistical analysis of von Frey results. $P<0.05$ was accepted as statistical significance.

Representative results are presented in FIG. 8. As shown in FIG. 8A-FIG. 8H, Runx1-deficient mice exhibited pain behavioral deficits. Behavioral sensitivity of control Runx1$^{F/F}$ mice (open bars) and Runx1$^{-/-}$ mice (hatched bars) in tests of heat (hotplate, FIG. 8A-FIG. 8B), cold (acetone evaporation, FIG. 8C), chemical pain (capsaicin-induced pain, FIG. 8D), and mechanical pain (von Frey, FIG. 8E, or pin prick stimuli, FIG. 8F) are shown. n=19 for control Runx1$^{F/F}$ and n=16 for Runx1$^{-/-}$ groups, *P<0.05, P<0.01 and *P<0.001.

Runx1-deficient mice exhibited a markedly diminished response to a noxious cold (acetone evaporation) stimulus (FIG. 8C). In addition, Runx1-deficient mice exhibited a significantly delayed reaction time to a noxious heat stimulus (50° C. and 52° C. hot plate) that was most evident at the lowest stimulus temperature (FIG. 8A-FIG. 8B). These findings could reflect loss of expression of those TRP channels implicated in noxious cold and heat pain sensitivity (Jordt S E et al. (2003) *Curr Opin Neurobiol* 13:487-92). Alternatively, the defects in responsiveness to thermal noxious stimuli could result from alterations in connectivity (FIG. 7). Regardless, the findings establish a requirement for Runx1 activity in sensory neurons for the detection of acute thermal noxious stimuli.

Mechanical pain, however, was not markedly changed by the loss of Runx1 function. Thus, the sensitivity of Runx1$^{-/-}$ mice to noxious mechanical stimuli was not significantly altered in this set of experiments (FIG. 8E and FIG. 8F), implying that Runx1-independent channels/receptors are able to detect noxious mechanical stimuli. The absence of TRPA1 expression in Runx1$^{-/-}$ mice (FIG. 4A) also suggests that TRPA1 may not act as an exclusive mechanotransducer in nociceptors (Jordt S E et al. (2003) *Curr Opin Neurobiol* 13:487-92; Bandell M et al. (2004) *Neuron* 41:849-57) even though it has been reported to have a mechanotransduction role in the vestibular apparatus and cochlea. Corey D P et al. (2004) *Nature* 432:723-30.

Example 9

Runx1-Deficient Mice Exhibit Markedly Diminished Neuropathic Pain

Neuropathic pain represents a heightened pain sensitivity induced by peripheral nerve injury, and normally innocuous tactile stimuli can evoke pain or pain-like withdrawal response, a phenomenon termed mechanical allodynia. Woolf C (2004) *Life Sci* 74:2605-10. Abnormal activation of Ret$^+$ class nociceptors may possibly underlie peripheral neuropathic pain. In order to assess if neuropathic pain is affected in Runx1$^{-/-}$ mice, experiments were performed in mice using the spared nerve injury (SNI) model.

The spared nerve injury (SNI) model was performed on Runx1$^{-/-}$ and control Runx1$^{F/F}$ mice as described for rats. Decosterd I et al. (2000) *Pain* 87:149-58. Briefly, animals were anesthetized using isoflurane (3% induction, 2% maintenance). An incision was made on the lateral thigh and the underlying muscle separated to expose the sciatic nerve. The three terminal branches of the sciatic nerve (tibial, common peroneal, and sural nerves) were carefully separated while minimizing any contact with or stretching of the sural nerve. The tibial and common peroneal nerves were then individually ligated with 6.0 silk and cut distally. 2-3 mm of each nerve distal to the ligation was removed. The muscle incision was closed using silk sutures and the skin with surgical staples.

Animals were placed on an elevated wire grid and the lateral plantar surface of the hindpaw stimulated using von Frey monofilaments (0.0174-4.57 g). The withdrawal threshold for the von Frey assay was determined as the filament at which the animal withdrew its paw at least twice in 10 applications.

All animals were acclimatized to the behavioral testing apparatus on at least three 'habituation' sessions. Following habituation, at least two baseline measures were obtained on two separate occasions the week before surgery. Following the surgical procedures (day 0), the behavioral tests were performed at defined intervals. The tester was blinded to the genotype of each animal.

Baseline data (and all non-procedural testing data) was taken as the mean of two tests performed. Post-surgery behavioral data were analyzed by Student's T-test when comparing two groups (Graphpad Prism, Graphpad, San Diego, Calif.) and 2-way repeated measures ANOVA followed by Bonferroni's post-test for time courses of two or more groups (R, v. 1.7.0, R Development Core Team, Vienna, Austria). $P<0.05$ was accepted as statistical significance.

Representative results are shown in FIG. 8G, where n=6 for each group. As shown in FIG. 8G, in control $Runx1^{F/F}$ mice, nerve injury induced mechanical allodynia, indicated by a substantial lowering of the paw withdrawal threshold (ANOVA interaction: $F(8,80)=3.14$, $P<0.01$). After SNI in $Runx1^{-/-}$ mice, no change in paw withdrawal threshold was detected ($P>0.05$), indicating an absence of mechanical allodynia. These results demonstrate that Runx1 function is necessary for the manifestation of neuropathic pain responses.

Example 10

Runx1-Deficient Mice Exhibit Diminished Response to Inflammatory Pain

Inflammatory pain occurs in response to peripheral tissue inflammation. Snider W D et al. (1998) *Neuron* 20:629-32. In order to assess if Runx1 function is involved in establishment of inflammatory pain responses, mechanical allodynia was monitored after intraplantar injection of complete Freund's adjuvant (CFA).

For CFA-mediated inflammation, mice were briefly anesthetized with isoflurane (2-3 min) and 15 ml of CFA injected into the plantar surface of the left hindpaw.

Animals were placed on an elevated wire grid and the lateral plantar surface of the hindpaw stimulated using von Frey monofilaments (0.0174-4.57 g). The withdrawal threshold for the von Frey assay was determined as the filament at which the animal withdrew its paw at least twice in 10 applications.

All animals were acclimatized to the behavioral testing apparatus on at least three 'habituation' sessions. Following habituation, at least two baseline measures were obtained on two separate occasions. Following the CFA injection, the von Frey tests were performed as described above. The tester was blinded to the genotype of each animal. n=13 control $Runx1^{F/F}$ mice and n=10 $Runx1^{-/-}$ mice. Log data was used for statistical analysis of von Frey results. $P<0.05$ was accepted as statistical significance. Representative results are depicted in FIG. 8H.

As shown in FIG. 8H, although both wild-type and $Runx1^{-/-}$ mice developed mechanical allodynia in the inflamed hindpaw (FIG. 8H), the degree of allodynia was less in $Runx1^{-/-}$ than in control $Runx1^{F/F}$ mice (ANOVA interaction: $F(1,21)=23.556$, $P<0.001$). These results indicate Runx1 also has a role in the development of inflammatory pain.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages of the invention are not necessarily encompassed by each embodiment of the invention.

All references, patents and patent publications that are recited in this application are incorporated in their entirety herein by reference.

What is claimed is:

1. A method for identifying a candidate inhibitor of runt-related transcription factor 1 (Runx1)-mediated expression of a nociceptive receptor or ion channel, the method comprising
contacting a test cell that expresses Runx1 and comprises a nucleic acid encoding a nociceptive receptor or ion channel operatively linked to a Runx1-sensitive promoter, with a test agent;
measuring a test amount of expression of the nociceptive receptor or ion channel;
comparing the test amount of expression of the nociceptive receptor or ion channel to a control amount of expression of the nociceptive receptor or ion channel measured in a control cell that expresses Runx1 and comprises the nucleic acid encoding the nociceptive receptor or ion channel operatively linked to the Runx1-sensitive promoter, wherein the control cell is not contacted with the test agent; and
identifying the test agent as a candidate inhibitor of Runx1-mediated expression of a nociceptive receptor or ion channel when the control amount of expression of the nociceptive receptor or ion channel is greater than the test amount of expression of the nociceptive receptor or ion channel.

2. The method of claim 1, wherein the nucleic acid encoding the nociceptive receptor or ion channel operatively linked to the Runx1-sensitive promoter encodes a nociceptive receptor or ion channel chosen from TRPC3, TRPM8, TRPA1, Mrgprd, P2X3, Nav1.9/SNS2, TRPV1, TRPV2, Mrgpra1, Mrgpra2, Mrgpra3, Mrgpra6, Mrgprb4, Mrgprb5 and any combination thereof.

3. The method of claim 1, wherein the test cell comprises a Runx1 expression vector.

4. The method of claim 1, wherein the control cell comprises a Runx1 expression vector.

5. The method of claim 1, wherein the test amount of expression of the nociceptive receptor or ion channel and the control amount of expression of the nociceptive receptor or ion channel are corresponding amounts of transcript for the nociceptive receptor or ion channel.

6. The method of claim 1, wherein the test amount of expression of the nociceptive receptor or ion channel and the control amount of expression of the nociceptive receptor or ion channel are corresponding amounts of protein for the nociceptive receptor or ion channel.

7. The method of claim 1, wherein the nucleic acid encoding the nociceptive receptor or ion channel operatively linked to the Runx1-sensitive promoter is part of an expression vector.

8. The method of claim 1, wherein the control cell is a dorsal root ganglion cell derived from a Runx1F/F; Wnt1-Cre mouse.

9. The method of claim 1, wherein the test compound is selected from the group consisting of small molecules, peptides, nucleic acids, and any combination thereof.

10. The method of claim 1, wherein the test compound is a small molecule.

11. The method of claim 1, wherein the test compound is a nucleic acid.

12. The method of claim 1, wherein the test compound inhibits expression of Runx1.

13. A method for identifying a candidate agent for use in inhibiting neuropathic pain, the method comprising
contacting a test cell that expresses runt-related transcription factor 1 (Runx1) and comprises a nucleic acid encoding a nociceptive receptor or ion channel operatively linked to a Runx1-sensitive promoter, with a test agent;
measuring a test amount of expression of the nociceptive receptor or ion channel;
comparing the test amount of expression of the nociceptive receptor or ion channel to a control amount of expression of the nociceptive receptor or ion channel measured in a control cell that expresses Runx1 and comprises the nucleic acid encoding the nociceptive receptor or ion channel operatively linked to the Runx1-sensitive promoter, wherein the control cell is not contacted with the test agent; and
identifying the test agent as a candidate agent for use in inhibiting neuropathic pain when the control amount of expression of the nociceptive receptor or ion channel is greater than the test amount of expression of the nociceptive receptor or ion channel.

14. The method of claim 13, wherein the nucleic acid encoding the nociceptive receptor or ion channel operatively linked to the Runx1-sensitive promoter encodes a nociceptive receptor or ion channel chosen from TRPC3, TRPM8, TRPA1, Mrgprd, P2X3, Nav1.9/SNS2, TRPV1, TRPV2, Mrgpra1, Mrgpra2, Mrgpra3, Mrgpra6, Mrgprb4, Mrgprb5 and any combination thereof.

15. The method of claim 13, wherein the test cell comprises a Runx1 expression vector.

16. The method of claim 13, wherein the control cell comprises a Runx1 expression vector.

17. The method of claim 13, wherein the test amount of expression of the nociceptive receptor or ion channel and the control amount of expression of the nociceptive receptor or ion channel are corresponding amounts of transcript for the nociceptive receptor or ion channel.

18. The method of claim 13, wherein the test amount of expression of the nociceptive receptor or ion channel and the control amount of expression of the nociceptive receptor or ion channel are corresponding amounts of protein for the nociceptive receptor or ion channel.

19. The method of claim 13, wherein the nucleic acid encoding the nociceptive receptor or ion channel operatively linked to the Runx1-sensitive promoter is part of an expression vector.

20. The method of claim 13, wherein the control cell is a dorsal root ganglion cell derived from a Runx1F/F; Wnt1-Cre mouse.

21. The method of claim 13, wherein the test compound is selected from the group consisting of small molecules, peptides, nucleic acids, and any combination thereof.

22. The method of claim 13, wherein the test compound is a small molecule.

23. The method of claim 13, wherein the test compound is a nucleic acid.

24. The method of claim 13, wherein the test compound inhibits expression of Runx1.

* * * * *

UNITED STATES PATENT AND TRADEMARK OFFICE
CERTIFICATE OF CORRECTION

| | | |
|---|---|---|
| PATENT NO. | : 8,268,572 B2 | Page 1 of 1 |
| APPLICATION NO. | : 11/884800 | |
| DATED | : September 18, 2012 | |
| INVENTOR(S) | : Qiufu Ma et al. | |

It is certified that error appears in the above-identified patent and that said Letters Patent is hereby corrected as shown below:

On the Title Page, Item (57), the Abstract should read:

Methods are provided for identifying candidate agents for use in inhibiting expression of certain receptors and ion channels in nociceptors. Also provided are methods for identifying candidate agents for use in inhibiting neuropathic and other types of pain.

Signed and Sealed this
Thirteenth Day of November, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
tatctcacgt actgacggtg                    20

<210> SEQ ID NO 2
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 2
ctagtctaga ctaatcgcca tcttccagc           29

<210> SEQ ID NO 3

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
gagtcccagc tgtcaattcc                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
ggtgatggtc agagtgaagc                                              20
```